(12) United States Patent
Burtea

(10) Patent No.: US 10,539,480 B2
(45) Date of Patent: Jan. 21, 2020

(54) FREQUENCY SUB-BAND LEAK DETECTION

(71) Applicant: Mueller International, LLC, Atlanta, GA (US)

(72) Inventor: Valentin Mircea Burtea, Toronto (CA)

(73) Assignee: Mueller International, LLC, Atlanta, GA (US)

( * ) Notice: Subject to any disclaimer, the term of this patent is extended or adjusted under 35 U.S.C. 154(b) by 76 days.

(21) Appl. No.: 15/796,108

(22) Filed: Oct. 27, 2017

(65) Prior Publication Data

US 2019/0128767 A1 May 2, 2019

(51) Int. Cl.
| | | |
|---|---|---|
| *G01M 3/24* | (2006.01) | |
| *G01N 29/07* | (2006.01) | |
| *G01B 17/02* | (2006.01) | |
| *G01N 29/44* | (2006.01) | |
| *G01N 29/22* | (2006.01) | |
| *G01F 23/296* | (2006.01) | |
| *G01F 23/22* | (2006.01) | |

(52) U.S. Cl.
CPC .............. *G01M 3/243* (2013.01); *G01B 17/02* (2013.01); *G01N 29/07* (2013.01); *G01N 29/222* (2013.01); *G01N 29/4418* (2013.01); *G01F 23/22* (2013.01); *G01F 23/2962* (2013.01); *G01F 23/2965* (2013.01); *G01F 23/2968* (2013.01)

(58) Field of Classification Search
CPC .......... G01M 3/243; G01M 3/00; G01M 3/24; G01M 3/2807; G01N 29/4472; G01F 23/2968; G01F 23/22; G01F 23/2965; G01F 23/2962; B06B 1/0644
See application file for complete search history.

(56) References Cited

U.S. PATENT DOCUMENTS

| | | | |
|---|---|---|---|
| 3,673,856 A | 7/1972 | Panigati | |
| 4,083,229 A | 4/1978 | Anway | |
| 4,289,019 A | 9/1981 | Claytor | |

(Continued)

FOREIGN PATENT DOCUMENTS

| | | |
|---|---|---|
| CA | 2397174 | 8/2008 |
| CN | 105844051 | 8/2016 |

(Continued)

OTHER PUBLICATIONS

Hunaidi, Osama; Issue Notification for U.S. Appl. No. 11/766,288, filed Jun. 21, 2007, dated Sep. 22, 2010, 1 pg.

(Continued)

*Primary Examiner* — David A Rogers
(74) *Attorney, Agent, or Firm* — Taylor English Duma LLP

(57) ABSTRACT

Examples of analyzing data for a distribution pipe network within a fluid distribution system are disclosed. In one example implementation according to aspects of the present disclosure, a method for analyzing data for a distribution pipe network within a fluid distribution system includes: receiving acoustic data from a plurality of nodes for a plurality of pipe segments; determining a characteristic frequency range for each pipe segment; decomposing the characteristic frequency range into a plurality of frequency sub-bands; building a leak sensitivity model based on the plurality of frequency sub-bands; and implementing a correlation schedule with the plurality of nodes based on a selection of the plurality of frequency sub-bands.

20 Claims, 19 Drawing Sheets

(56) References Cited

U.S. PATENT DOCUMENTS

| | | | | |
|---|---|---|---|---|
| 4,457,163 | A | * | 7/1984 | Jackle .................... G01N 29/14 73/40.5 A |
| 4,462,249 | A | | 7/1984 | Adams |
| 4,543,817 | A | * | 10/1985 | Sugiyama ............. G01M 3/243 73/40.5 A |
| 4,612,620 | A | * | 9/1986 | Davis ....................... G01H 1/00 702/184 |
| 5,038,614 | A | | 8/1991 | Bseisu |
| 5,052,215 | A | | 10/1991 | Lewis |
| 5,117,676 | A | * | 6/1992 | Chang .................... G01M 3/243 73/40.5 A |
| 5,272,646 | A | * | 12/1993 | Farmer ............... G01M 3/2815 340/605 |
| 5,319,956 | A | | 6/1994 | Bogle et al. |
| 5,333,501 | A | * | 8/1994 | Okada .................... G01M 3/243 73/40.5 A |
| 5,416,724 | A | | 5/1995 | Savic |
| 5,433,104 | A | * | 7/1995 | Kunze ..................... G01M 3/24 73/40.5 A |
| 5,461,906 | A | | 10/1995 | Bogle et al. |
| 5,502,652 | A | * | 3/1996 | Hoggatt .................. G01F 1/662 702/136 |
| 5,531,099 | A | * | 7/1996 | Russo .................... G01M 3/243 73/40.5 A |
| 5,548,530 | A | * | 8/1996 | Baumoel ............... G01M 3/243 702/48 |
| 5,708,195 | A | * | 1/1998 | Kurisu ...................... F17D 5/02 340/605 |
| 5,974,862 | A | | 11/1999 | Lander |
| 6,003,376 | A | * | 12/1999 | Burns ....................... G01S 3/808 73/584 |
| 6,138,512 | A | | 10/2000 | Roberts |
| 6,267,000 | B1 | * | 7/2001 | Harper ..................... G01M 3/24 73/40 |
| 6,435,030 | B1 | | 8/2002 | Gysling |
| 6,453,247 | B1 | | 9/2002 | Hunaidi |
| 6,561,032 | B1 | | 5/2003 | Hunaidi |
| 6,626,042 | B2 | * | 9/2003 | Havlena .................... G01F 1/34 367/81 |
| 6,725,705 | B1 | * | 4/2004 | Huebler ................ G01M 3/243 702/51 |
| 7,007,545 | B1 | * | 3/2006 | Martinek .............. G01M 3/243 73/40.5 A |
| 7,203,322 | B1 | | 4/2007 | Bostock |
| 7,328,618 | B2 | | 2/2008 | Hunaidi |
| 7,423,931 | B2 | * | 9/2008 | Martin, II ............... H04B 13/00 340/870.01 |
| 7,668,670 | B2 | * | 2/2010 | Lander .................. G01M 3/243 340/605 |
| 7,810,378 | B2 | | 10/2010 | Hunaidi |
| 7,856,864 | B2 | * | 12/2010 | McEwan ............. F16L 55/1003 73/40.5 R |
| 8,261,776 | B2 | * | 9/2012 | Catron .................. G05D 7/0635 137/2 |
| 8,342,006 | B2 | * | 1/2013 | Getto .................... G01M 3/2807 73/40 |
| 8,665,101 | B2 | * | 3/2014 | Solomon ............... G01M 3/243 340/605 |
| 9,053,519 | B2 | | 6/2015 | Scolnicov |
| 9,287,963 | B2 | * | 3/2016 | Parish ..................... H04B 7/14 |
| 9,939,344 | B2 | * | 4/2018 | Bracken ................ G01M 3/243 |
| 10,039,018 | B2 | * | 7/2018 | Splitz ....................... H04W 4/70 |
| 10,132,823 | B2 | * | 11/2018 | Giunta ....................... G01S 5/22 |
| 10,175,135 | B2 | * | 1/2019 | Dintakurt ................. G01M 3/00 |
| 10,209,225 | B2 | * | 2/2019 | Perrier .................... G01M 3/00 |
| 10,330,560 | B2 | * | 6/2019 | Yung ........................ G01M 3/28 |
| 2006/0283251 | A1 | | 12/2006 | Hunaidi |
| 2008/0078247 | A1 | | 4/2008 | Hunaidi |
| 2008/0314122 | A1 | | 12/2008 | Hunaidi |
| 2009/0250125 | A1 | * | 10/2009 | Howitt ...................... E03F 7/00 137/551 |
| 2011/0161037 | A1 | | 6/2011 | Sutherland |
| 2013/0213482 | A1 | | 8/2013 | Schuberth |
| 2013/0281008 | A1 | * | 10/2013 | Parish ...................... H04B 7/14 455/7 |
| 2014/0121999 | A1 | * | 5/2014 | Bracken ................ G01M 3/243 702/51 |
| 2015/0300907 | A1 | | 10/2015 | Giunta |
| 2016/0252422 | A1 | | 9/2016 | Howitt |
| 2016/0290974 | A1 | * | 10/2016 | Coleman ................ G01N 29/04 |
| 2016/0370325 | A1 | * | 12/2016 | Yusuf .................... G01N 29/032 |
| 2017/0064702 | A1 | | 3/2017 | Li et al. |
| 2017/0307466 | A1 | | 10/2017 | Brennan, Jr. et al. |
| 2018/0306755 | A1 | * | 10/2018 | Perrier .................... G01M 3/00 |
| 2019/0128766 | A1 | | 5/2019 | Burtea et al. |

FOREIGN PATENT DOCUMENTS

| | | |
|---|---|---|
| DE | 4211038 | 10/1993 |
| EP | 0711986 | 6/1995 |
| EP | 1077370 | 2/2001 |
| FR | 2439990 | 5/1980 |
| GB | 2250820 | 6/1992 |
| GB | 2269900 | 2/1994 |
| GB | 2367362 | 4/2002 |
| GB | 2421311 | 6/2006 |
| JP | 59170739 | 9/1984 |
| JP | 60111132 | 6/1985 |
| JP | 11201859 | 7/1999 |
| WO | 0151904 | 7/2001 |
| WO | 2019083768 | 5/2019 |

OTHER PUBLICATIONS

Hunaidi, Osama; Non-Final Office Action for U.S. Appl. No. 11/766,288, filed Jun. 21, 2007, dated Jan. 20, 2010, 50 pgs.

Hunaidi, Osama; Notice of Allowance for U.S. Appl. No. 11/766,288, filed Jun. 21, 2007, dated Jun. 24, 2010, 8 pgs.

Hunaidi, Osama; Non-final Office Action for U.S. Appl. No. 09/482,317, filed Jan. 14, 2000, dated Dec. 17, 2001, 6 pgs.

Hunaidi, Osama; Notice of Allowance for U.S. Appl. No. 09/482,317, filed Jan. 14, 2000, dated May 13, 2002, 4 pgs.

Peter, Russo Anthony; European Search Report for Patent Application No. EP95307807, filed Nov. 1, 1995, dated Jul. 22, 1998, 5 pgs.

Almeida, et al.; Article entitled: "On the Acoustic Filtering of the Pipe and Sensor in a Buried Plastic Water Pipe and its Effect on Leak Detection: An Experimental Investigation", Sensors, Copyright 2014, 16 pgs.

Article Entitled: "Conjugate Quadrature Filters (CQF)", located at <www.dsprelated.com/freebooks/sasp/Conjugate_Quadrature_Filters_CQF.html> accessed on Jun. 30, 2017, 6 pgs.

Article Entitled: "Quadrature Mirror Filters (QMF)", located at <www.dsprelated.com/freebooks/sasp/Quadrature_Mirror_Filters_QMF.html> accessed on Jun. 30, 2017, 5 pgs.

De Almeida, et al.; Article entitled: "Measurement of Wave Attenuation in Buried Plastic Water Distribution Pipes", Journal of Mechanical Engineering, published on Apr. 1, 2014, 9 pgs.

Mukherjee, Amar, et al.; Article Entitled: "Subband Coding", Lecture Notes of Image Compression and Video Compression Series., 2005, 49 pgs.

Oelze, et al.; Article entitled: "Measurement of Attenuation and Speed of Sound in Soils", Soil Sci. Soc. Am. J., vol. 66, May-Jun. 2002, 9 pgs.

Burtea, Valentin Mircea; International Search Report for PCT Application No. PCT/USI8/55976, filed Oct. 16, 2018, dated Dec. 4, 2018, 8 pgs.

* cited by examiner

900

Correlation Schedule/Schema

| Bands | Frequency Times/Month |
|---|---|
| B2-B3 | 4 |
| B3-B4 | 9 |
| B4-B5 | 8 |
| B5-B6 | 4 |
| B6-B7 | 2 |
| B7-B8 | 1 |
| Total | 28 |

*FIG. 9*

FREQUENCY SUB-BAND LEAK DETECTION

BACKGROUND

A utility provider may install and maintain infrastructure to provide utility services to its customers. For example, a water utility provider may implement a fluid distribution system to distribute water to its customers. Metering devices may be utilized by the utility provider to determine consumption of the provided utility (e.g., water, electricity, gas, etc.). The utility provider may implement various devices or computing nodes throughout the fluid distribution system to monitor the status of the fluid distribution system. However, due to the rapidly escalating costs of potable water, the scarcity of fresh water supplies, the increasing costs for water treatment and distribution, and the potential for costly damage to subsurface infrastructure, minimizing leaks in water distribution systems is a goal of both public and private water distribution utilities. If a leak is not particularly conspicuous, it may go undetected for months at a time without repair. It is therefore important to be able to detect leaks early.

Several techniques for leak detection currently exist, however, more utility providers are utilizing leak detection systems utilizing acoustic monitoring to perform leak detection. These acoustic monitoring systems are good screening tools for detecting widespread corrosion and wall loss, they are non-intrusive, and generally they are low cost. However, current techniques utilizing acoustic monitoring require large amounts of data to be sent through a data network, affecting battery life at each computing node. Considering energy and data requirements, acoustic monitoring solutions may increase the cost of operations throughout the system.

SUMMARY

It is to be understood that this summary is not an extensive overview of the disclosure. This summary is exemplary and not restrictive, and it is intended to neither identify key or critical elements of the disclosure nor delineate the scope thereof. The sole purpose of this summary is to explain and exemplify certain concepts of the disclosure as an introduction to the following complete and extensive detailed description.

The present disclosure relates to collecting and analyzing data in a fluid distribution system. According to some aspects, a method for receiving and analyzing data for a distribution pipe network within a fluid distribution system comprises receiving acoustic data from a plurality of nodes for a plurality of pipe segments. A characteristic frequency range for each pipe segment is then determined. Further, the characteristic frequency range is decomposed into a plurality of frequency sub-bands, and a leak sensitivity model is built based on the plurality of frequency sub-bands. Finally, the method comprises implementing a correlation schedule with the plurality of nodes based on a selection of the plurality of frequency sub-bands.

According to further aspects, a system for receiving and analyzing data for a distribution pipe network within a fluid distribution system comprises a plurality of computing nodes and a computing host in communication with the plurality of computing nodes. The computing host is in communication with the fluid distribution system and configured to create a correlation schedule based on a selection of frequency sub-bands. The plurality of computing nodes are in communication with the computing host and configured to acquire acoustic data in the fluid distribution system. Each node is programmed to perform steps. The first step comprises downloading the correlation schedule. Then each node synchronizes time with a reference time, records an acoustic signal where each node records acoustic data at a same time and for a same duration, and reads the correlation schedule to determine a plurality of specific frequency sub-bands for each recording. Each node then selects the sub-band signal for each of the plurality of specific frequency sub-bands. Finally, each node decimates the specific sub-band signal for each of the plurality of specific frequency sub-bands, compresses the specific sub-band signal for each of the plurality of specific frequency sub-bands utilizing a quantization method, and transmits, as one file, a plurality of compressed sub-band signals to the computing host.

According to further aspects, a non-transitory computer-readable storage medium stores instructions that, when executed by a processing resource, cause the processing resource to perform steps. The first step comprises receiving acoustic data from a plurality of nodes for a plurality of pipe segments. A characteristic frequency range for each pipe segment is then determined. Further, the characteristic frequency range is decomposed into a plurality of frequency sub-bands, and a leak sensitivity model is built based on the plurality of frequency sub-bands. Finally, the last step comprises implementing a correlation schedule with the plurality of nodes based on a selection of the plurality of frequency sub-bands.

These and other features and aspects of the various aspects will become apparent upon reading the following Detailed Description and reviewing the accompanying drawings. Furthermore, other examples are described in the present disclosure. It should be understood that the features of the disclosed examples can be combined in various combinations. It should also be understood that certain features can be omitted while other features can be added.

BRIEF DESCRIPTION OF THE DRAWINGS

In the following Detailed Description, references are made to the accompanying drawings that form a part hereof, and that show, by way of illustration, specific aspects or examples. Any illustrated connection pathways in block and/or circuit diagrams are provided for purposes of illustration and not of limitation, and some components and/or interconnections may be omitted for purposes of clarity. The drawings herein are not drawn to scale. Like numerals represent like elements throughout the several figures.

FIG. 9 illustrates a table of a correlation schedule within a fluid distribution system according to examples of the present disclosure.

DETAILED DESCRIPTION

Figure 1:
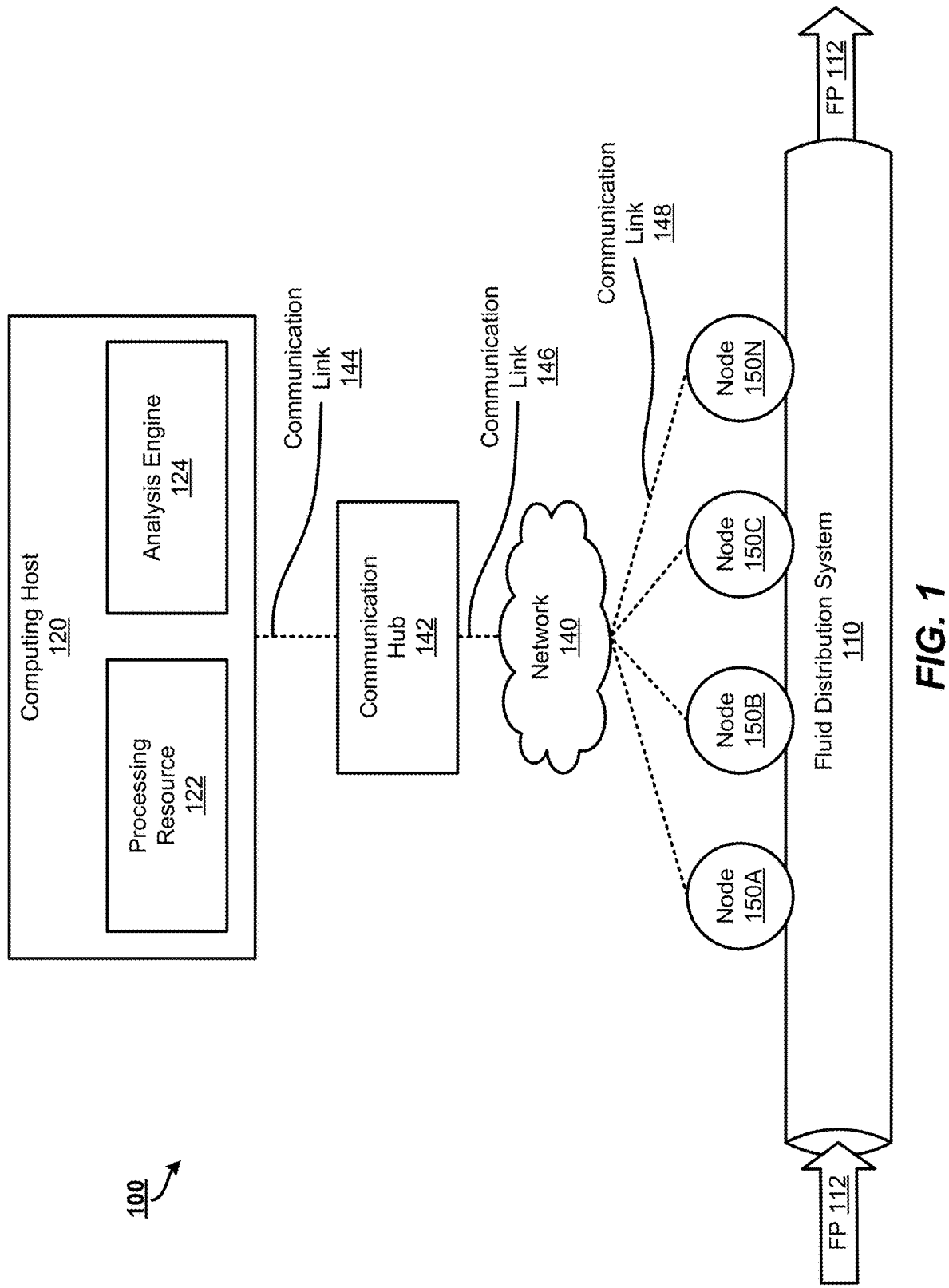
FIG. 1 illustrates a diagram of an environment to collect and analyze acoustic data for condition assessment and leak detection within a fluid distribution system according to examples of the present disclosure.

Various implementations are described below by referring to several examples of collecting and analyzing acoustic data in a fluid distribution system. In examples, the water utility provider may deploy devices (nodes) across the fluid distribution system to collect data relating to the network of pipes. One concern for water utility companies is the loss of water through leaks in the pipes. Not only do leaks waste clean potable water, but sometimes contaminants may be introduced into the water supply from outside the pipes. Leaking pipes may also cause damage to surrounding areas. Thus, the acoustic data collected by the nodes may be analyzed to detect leaks. Example implementations and variations are disclosed herein for analyzing data to detect leaks.

According to aspects described herein, as an acoustic propagation detection system is used to detect leaks in a given distribution pipe network, there are different factors and characteristics that are learned about the pipe network including the different soils, tuberculated pipes, incorrect data, and the like, that affect the efficacy of detecting leaks. Thus, there is a need to create a model capable of adapting through learning from discovered leaks; the model determines statistically which frequency ranges (sub-bands) are more sensitive to acoustic energy of leaks for a given pipe network. Using this model, the system implements a correlation schedule using an alternating frequency sub-bands scheme, to maximize system's sensitivity to leaks. There is also a need for an acoustic monitoring system that utilizes more efficient data collection and transmission techniques (e.g. transmitting partial information with minimum performance degradation) in order to reduce the amount of data transmitted through the network. The present disclosure enables reliable leak detection for a fluid distribution system by implementing a correlation schedule based on a selection of frequency sub-bands to reduce the amount of data transmitted through the network. The present disclosure addresses a problem for high volume data collection from nodes by decomposing the signal information into multiple frequency sub-bands and selecting to transmit more frequently those frequency sub-bands which are more sensitive to acoustic energy from leaks for a given distribution pipe network. According to aspects described herein, the system may prioritize those sub-bands that are more sensitive to leaks for a given pipe network, where a key aspect of the processes and systems described herein is then determining how to select those more important frequency sub-bands and transmit those bands more frequently than others. It would be understood by one skilled in the art as a data traffic shaping problem.

According to further aspects described herein, data compression utilizing quantization, such as 1-bit quantization (may be also referred to as clipping compression), may be used by the nodes before sending the acoustic signals to a host. Further, the benefits of the present disclosure may provide lower power consumption of the nodes, lower overall cost of operations, and lower data collection cost due to the reduction of the amount of data collected by the nodes and analyzed by the nodes and/or a computing host.

According to further aspects described herein, the present disclosure enables aggregation of multiple acoustic data samples taken at distinct times and utilizing correlation techniques for leak detection. The method involves recording one short signal per session; these short signals captured over multiple sessions may be aggregated into a long signal. The processing gain of the correlation method is related to the length of the signals: longer signals provide a better signal-to-noise ratio, thus a better detection. A leak with a strong acoustic energy will likely be detected immediately using a short recording, while a weak acoustic source may require processing over multiple sessions and is reported with a delay. This intention thus fits with a typical operational profile of an acoustic propagation detection system for detecting leaks, as a large leak should be fixed as soon as possible, while a weak leak is likely to have less priority.

If each node has a near-perfect time reference (i.e. global positioning system ("GPS")) then the signals may be aggregated directly. However, synchronization between nodes is not perfect and signal aggregation will require certain time corrections before aggregation. Data may also be reduced in size by filtering and compressing the data. Battery life of nodes for detecting leaks may be increased by reducing the frequency of data transmission sessions and the amount of transmitted data. These and other advantages will be apparent from the description that follows.

Figure 2:
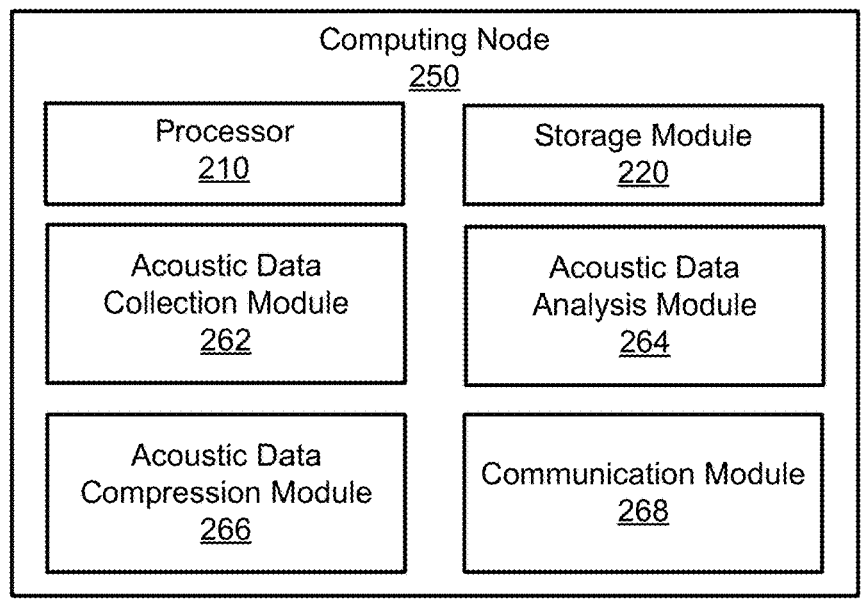
FIG. 2 illustrates a block diagram of a computing node to collect and analyze acoustic data for condition assessment and leak detection within a fluid distribution system according to examples of the present disclosure.
Figure 3:
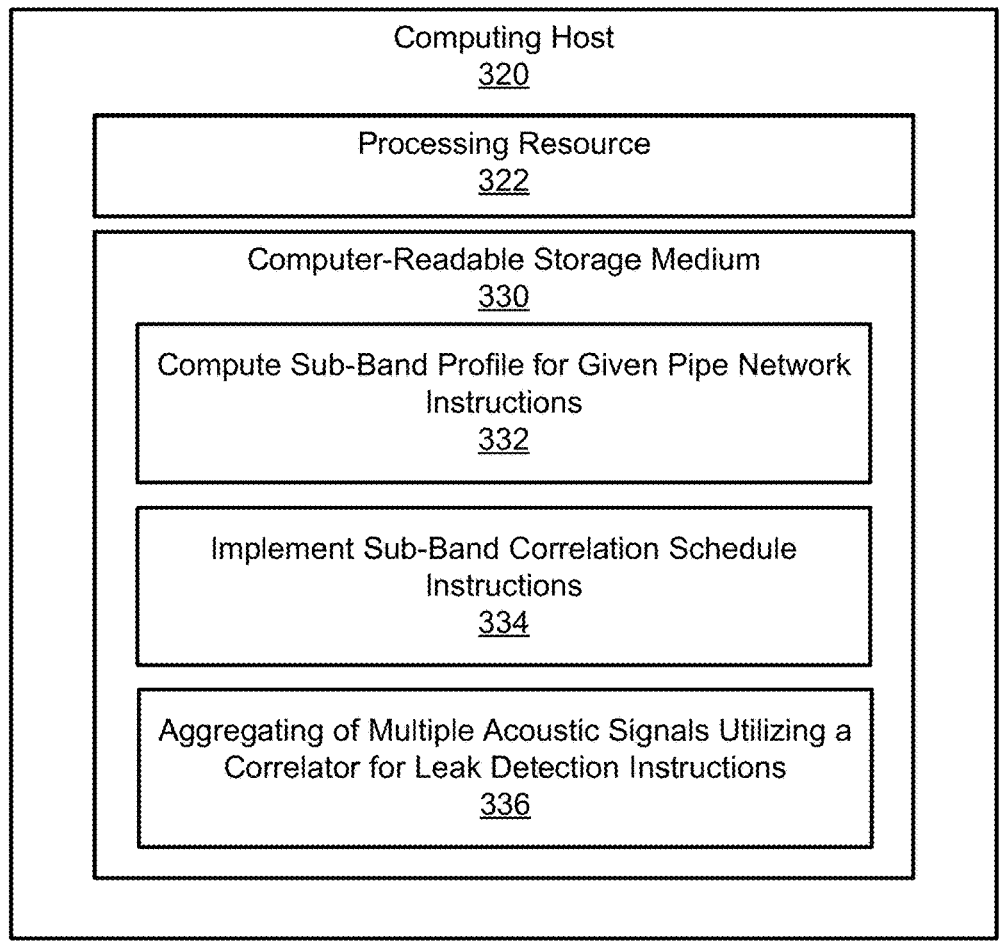
FIG. 3 illustrates a computing system including a computer-readable storage medium storing instructions to analyze the data collected within a fluid distribution system according to examples of the present disclosure.

FIGS. 1-3 illustrate particular components, modules, instructions, engines, etc. according to various examples as described herein. In different implementations, more, fewer, and/or other components, modules, instructions, engines, arrangements of components/modules/instructions/engines, etc. may be used according to the teachings described herein. In addition, various components, modules, engines, etc. described herein may be implemented as instructions stored on a computer-readable storage medium, as hardware modules, as special-purpose hardware (e.g., application specific hardware, application specific integrated circuits (ASICs), as embedded controllers, hardwired circuitry, etc.), or as some combination or combinations of these.

Generally, FIGS. 1-3 relate to components and modules of a computing system, such as computing host 120 of FIG. 1 and computing host 320 of FIG. 3 as well as components and modules of a computing node, such as computing nodes 150A-150N (also referred to herein generally as computing nodes 150) of FIG. 1 and computing node 250 of FIG. 2. It should be understood that the computing hosts and/or computing nodes may comprise any appropriate type of computing system and/or computing device, including for example smartphones, tablets, desktops, laptops, workstations, servers, smart monitors, smart televisions, digital signage, scientific instruments, retail point of sale devices, video walls, imaging devices, peripherals, networking equipment, wearable computing devices, metering devices, data collection devices, leak detecting devices, or the like.

FIG. 1 illustrates a diagram of an environment 100 to collect and analyze acoustic data within a fluid distribution system 110, according to examples of the present disclosure. As will be further described herein, computing nodes 150 of FIG. 1 collect and analyze acoustic data relating to the fluid distribution system 110. The acoustic data collected by the computing nodes 150 is transmitted to computing host 120 which performs analysis on the received data to compute a sub-band profile for a given pipe distribution network, determine and implement a sub-band correlation schedule, and aggregate multiple acoustic signals utilizing a correlator for leak detection.

As illustrated, the environment 100 comprises the fluid distribution system 110, which may further comprise various components such as pipes, hydrants, valve, couplers, corporation stops, metering devices, etc. Although illustrated as a pipe, it should be understood that the fluid distribution system 110 may be a plurality of pipes and/or pipe segments, such as pipes, hydrants, valves, couplers, corporation stops, metering devices, and the like, as well as suitable combinations thereof, and other fluid distribution system components connected together to form the fluid distribution system 110, of which the pipe is a portion.

Generally, the fluid distribution system 110 may be used to distribute fluids such as water to customers of a utility provider, for example. The fluid distribution system 110 may be partially or wholly subterraneous, or portions of the fluid distribution system 110 may be subterraneous, while other portions of the fluid distribution system 110 may be non-subterraneous (i.e., above ground). For example, a component of the fluid distribution system 110 may be partially or wholly subterraneous while another component (e.g., a hydrant, a valve, a testing device, etc.) connected to the first component and may be partially or wholly non-subterraneous. In other examples, the component may be partially subterraneous in that the component has portions exposed, such as to connect certain devices (e.g., computing nodes 150, a hydrant, a valve, a testing device, etc.) to the fluid distribution system 110.

The computing nodes 150 monitor certain aspects of the fluid distribution system 110 and/or aspects of a fluid flowing through the fluid distribution system 110, illustrated as fluid path 112 within the fluid distribution system 110. In examples, the computing nodes 150 can make direct contact with fluid path 112 within the fluid distribution system 110. In other examples, the computing nodes 150 are connected to a component of the fluid distribution system 110 and are not in contact with the fluid path 112. As illustrated in FIG. 1, the computing nodes 150 are connected to a pipe of the fluid distribution system 110. In examples, the connection may be direct and/or indirect. More particularly, the computing nodes 150 may be connected directly to a pipe of the fluid distribution system 110, such as through a hole drilled into the wall of the pipe or via a coupling member (not shown) of the pipe, thereby causing the computing nodes 150 (or a sensor of the computing nodes 150) to be in fluid communication with the fluid path 112. In another example, computing nodes 150 may be connected indirectly to the pipe, such as via another component in the fluid distribution system 110 (e.g., a hydrant, a valve, a coupler, a corporation stop, metering device, etc.). Although four computing nodes 150A-N are illustrated, it should be understood that any suitable number of computing nodes are possible in various examples. In examples, the computing nodes 150 are placed in or connected to existing components of the fluid distribution system 110, such as a fire hydrant. A computing node 150 may be connected to each fire hydrant within a fluid distribution system, for example, or may be placed within a certain distance of another node (e.g., within 500 feet, within 1500 feet, etc.)

The computing nodes 150 collect and analyze acoustic data concerning the fluid distribution system 110. For example, the computing nodes 150 may collect an acoustic data set synchronized with a known time reference for the purpose of detecting and locating a leak through correlation. The acoustic data set may be compressed before transmission. The acoustic data set may then be analyzed by computing host 120 to determine if a leak is present, compute a sub-band profile for a given pipe distribution network, determine and implement a sub-band correlation schedule, and/or aggregate multiple acoustic signals utilizing a correlator for leak detection.

As described below regarding FIG. 3, the computing nodes 150 may comprise various components, modules, engines, etc., such as a processor, a storage module, an acoustic data collection module, an acoustic data analysis module, an acoustic data compression module, a communication module, a power supply, a data transmitter, a data receiver, an antenna, etc. The data transmitter, data receiver, and/or antenna may be used to wirelessly transmit and/or receive signals, commands, and/or data to and from other devices, including the computing host 120 such as via the network 140 and a communications hub 142 across communication links 144-148.

The dotted lines of FIG. 1 illustrate communicative links between and among the computing nodes 150, the communication hub 142, and the computing host 120, including a communication link 144 (between the communication hub 142 and the computing host 120), a communication link 146 (between the communication hub 142 and a network 140), and communication links 148 (between the network 140 and the computing nodes 150). These links generally represent a network or networks that may comprise hardware components and computers interconnected by communications channels that enable sharing of resources and information. The network 140 may comprise one or more of a cable, wireless, fiber optic, or remote connection via a telecommunication link, an infrared link, a radio frequency link, a cellular link, a Bluetooth® link, or any other suitable connectors or systems that provide electronic communication. The network 140 may comprise, at least in part, an intranet, the internet, or a combination of both. The network 140 may also comprise intermediate proxies, routers, switches, load balancers, and the like. The paths followed by the network between the devices as depicted in FIG. 1 represent the logical communication links between the computing nodes 150, the communication hub 142, the network 140, and the computing host 120, not necessarily the physical paths or links between and among the devices.

The communication hub 142 may include a precise time reference such as global positioning system ("GPS") coordinates, and distributes the time information throughout the network. In other aspects, each computing node 150 may likewise include a time reference such as GPS coordinates. The computing nodes 150 collect and analyze acoustic data, as described herein. Each day, at specified times and periods, the computing nodes 150 may collect acoustic data and send information regarding the collected and analyzed data to the computing host 120.

The computing host 120 may comprise a processing resource 122 that represents generally any suitable type or form of processing unit or units capable of processing data or interpreting and executing instructions. The processing resource 122 may be one or more central processing units (CPUs), microprocessors, and/or other hardware devices suitable for retrieval and execution of instructions. The instructions may be stored, for example, on a memory resource, such as a computer-readable storage medium 330 of FIG. 3, which may comprise any electronic, magnetic, optical, or other physical storage device that stores executable instructions. Thus, the memory resource may be, for example, random access memory (RAM), electrically-erasable programmable read-only memory (EPPROM), a storage drive, an optical disk, and any other suitable type of volatile or non-volatile memory that stores instructions to cause a programmable processor (e.g., the processing resource 122) to perform the techniques described herein. In examples, the memory resource comprises a main memory, such as a RAM in which the instructions may be stored during runtime, and a secondary memory, such as a non-volatile memory in which a copy of the instructions is stored.

Additionally, the computing host 120 may comprise an analysis engine 124 which is configured to analyze acoustic data received from the computing nodes 150. In examples, the engine(s) described herein may be a combination of hardware and programming. The programming may be processor executable instructions stored on a tangible memory, and the hardware may comprise processing resource 122 for executing those instructions. Thus a memory resource (not shown) can be said to store program instructions that when executed by the processing resource 122 implement the engines described herein. Other engines may also be utilized to include other features and functionality described in other examples herein.

Alternatively or additionally, the computing host 120 may comprise dedicated hardware, such as one or more integrated circuits, Application Specific Integrated Circuits (ASICs), Application Specific Special Processors (ASSPs), Field Programmable Gate Arrays (FPGAs), or any combination of the foregoing examples of dedicated hardware, for performing the techniques described herein. In some implementations, multiple processing resources (or processing resources utilizing multiple processing cores) may be used, as appropriate, along with multiple memory resources and/or types of memory resources.

The analysis engine 124 is configured to perform various analyses of the data received from the computing nodes 150. For example, each day, when the computing nodes 150 send information regarding the collected and analyzed data to the computing host 120, the computing host 120 analyzes the received data. Objectives of the analysis are to compute a sub-band profile for a given pipe distribution network, determine and implement a sub-band correlation schedule, and aggregate multiple acoustic signals utilizing a correlator for leak detection. The analysis engine 124 may determine adjacencies among the computing nodes 150 and perform correlation of the acoustic data for adjacent nodes (e.g., nodes within adjacencies). The correlation may include analyzing acoustic data received from adjacent nodes. According to some aspects, the correlation analysis may use any known method in the art. An exemplary correlation analysis is further described herein for method 1200, FIG. 12. The computing host 120 may comprise additional engines, such as a data receiving engine to receive data from the computing nodes 150. The data may comprise raw acoustic data, and compressed acoustic data.

Although not shown in FIG. 1, it should be appreciated that the computing host 120 may comprise additional components. For example, the computing host 120 may comprise a display. The display may comprise a monitor, a touchscreen, a projection device, and/or a touch/sensory display device. The display may display data in the form of text, images, and other appropriate graphical content. The computing host 120 may further comprise a network interface to enable the computing host 120 to communicate via the communication link 148 with the computing nodes 150, with additional computing nodes, with other computing systems, and/or with other suitable devices. The computing host 120 may further implement a web server and a corresponding web application that allows multiple users to visualize the aforementioned data and configure the system remotely, over the network. The computing host 120 also implements a notification system that may notify users of a relevant event. The computing host 120 may also comprise any suitable input and/or output device, such as a mouse, keyboard, printer, external disk drive, touchscreen, microphone, or the like. The computing host 120 may also comprise an antenna (not shown) to wirelessly transmit and/or receive signals, commands, and/or data to and from other devices, including the computing nodes 150 such as via the communication hub 142 and the network 140 across the communication links 144-148.

FIG. 2 illustrates a block diagram of a computing node 250 to collect and analyze acoustic data within a fluid distribution system, such as fluid distribution system 110, according to examples of the present disclosure. The computing node 250 may represent any of computing nodes 150 of FIG. 1 and/or the computing nodes 450 illustrated in FIG. 4. The computing node 250 monitors certain aspects of the fluid distribution system and/or aspects of a fluid flowing through the fluid distribution system. In examples, the computing node 250 is in fluid communication with the fluid path 112 within the fluid distribution system. In other examples, the computing node 250 is connected to a component of the fluid distribution system that is not in fluid communication with the fluid path 112.

In examples, the computing node 250 may comprise various components, modules, engines, etc., such as a processor 210, a storage module 220, an acoustic data collection module 262, an acoustic data analysis module 264, an acoustic data compression module 266, and a communications module 268. The processor 210 may comprise one or more of a microcontroller unit (MCU), a digital signal processor (DSP), and other processing elements.

The storage module 220 may include flash memory, read-only memory (ROM), random access memory (RAM), or other types of memory. The storage module 220 may comprise a database for storing acoustic data collected by the acoustic data collection module 262. The database may include frequency bins for storing current acoustic data as well as historic data collected over several days. According to some aspects, the processor 210 may be configured to utilize the stored acoustic data to detect the presence or probability of leaks, bursts, or tampering activity.

The acoustic data collection module 262 may collect a first acoustic data during a first session at the computing node 250. The acoustic data collection module 262 also collects a second acoustic data during a second session at the computing node 250. The acoustic data may be collected using a sensor or sensors of the computing node 250. Although not illustrated, the computing node 250 may comprise a piezoelectric sensor, hydrophone, or other similar sensor to detect an acoustic signal. The acoustic signal is then collected by the acoustic data collection module 262 as acoustic data (e.g., first acoustic data, second acoustic data, etc.). According to further aspects, the acoustic data analysis module 264 may analyze the acoustic data by comparing the collected second acoustic data to reference acoustic data, as well as perform other data analysis on the acoustic data as described herein.

The acoustic data compression module 266 filters and compresses the collected acoustic data. The compressing may comprise clipping the amplitude of the raw acoustic data of an acoustic data recording to +1 for positive amplitude values and −1 for negative amplitude values. This compression may reduce the amount of bits required (e.g. each 16-bit raw sample becomes a 1-bit clipped sample, achieving a compression rate of 16:1, also known as 1-bit quantization).

The communication module 268 may transmit the acoustic data to the computing host (e.g., computing host 120 of FIG. 1 and/or computing host 320 of FIG. 3). The communication module 268, which may comprise a data receiver, a data transmitter, a data transceiver, and/or an antenna may be used to wirelessly transmit and/or receive signals, commands, and/or data to and from other devices, including the computing host via a network and/or a communications hub across a communication link or links. According to additional aspects, the computing node 250 may comprise other components which, although not illustrated, may comprise a power supply, a data receiver, an antenna, an input device, additional sensors, and the like.

FIG. 3 illustrates a computing system, such as computing host 320, including a computer-readable storage medium 330 storing instructions 332-336 to analyze data collected within a fluid distribution system according to examples of the present disclosure. The computer-readable storage medium 330 is non-transitory in the sense that it does not encompass a transitory signal but instead is made up of one or more memory components configured to store the instructions 332-336. The computer-readable storage medium 330 may be representative of a memory resource and may store machine executable instructions 332-336, which are executable on a computing system such as computing host 120 of FIG. 1 as well as the computing host 320 of FIG. 3 in conjunction with processing resource 322.

In the example shown in FIG. 3, the instructions 332-336 compute the sub-band profile for given pipe network instructions 332, implement sub-band correlation schedule instructions 334, and aggregating of multiple acoustic signals utilizing a correlator for leak detection instructions 336. The instructions 332-336 of the computer-readable storage medium 330 may be executable so as to perform the techniques described herein, including the functionality described regarding the method 500A of FIG. 5A, the method 500B of FIG. 5B, and the method 1200 of FIG. 12.

Figure 5A:
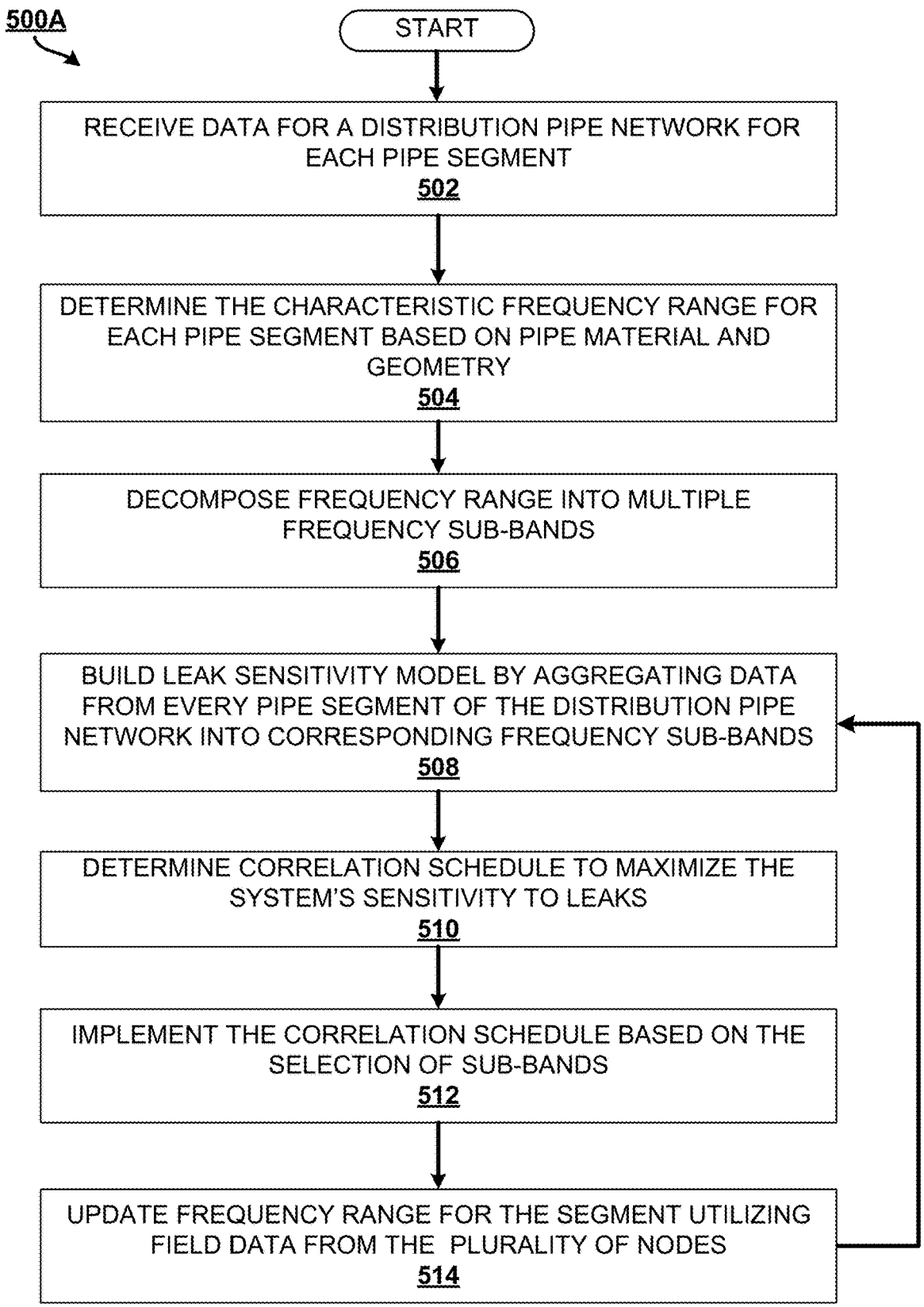
FIGS. 5A-5B illustrate flow diagrams of methods to analyze data collected within a fluid distribution system and to determine and implement a correlation schedule to maximize the system's sensitivity to leaks based on frequency sub-bands.

For example, the compute sub-band profile for given pipe network instructions 332 may correspond to blocks 502-514 of FIG. 5A. The implement sub-band correlation schedule instructions 334 may correspond to blocks 520-546 of FIG. 5B. Finally, the aggregating of multiple acoustic signals utilizing a correlator for leak detection instructions 336 may correspond to blocks 1202-1210 of FIG. 12. The functionality of these instructions 332-336 is described below with reference to the functional blocks of FIGS. 5A, 5B, and 12, respectively, but should not be construed as so limiting.

Figure 4:
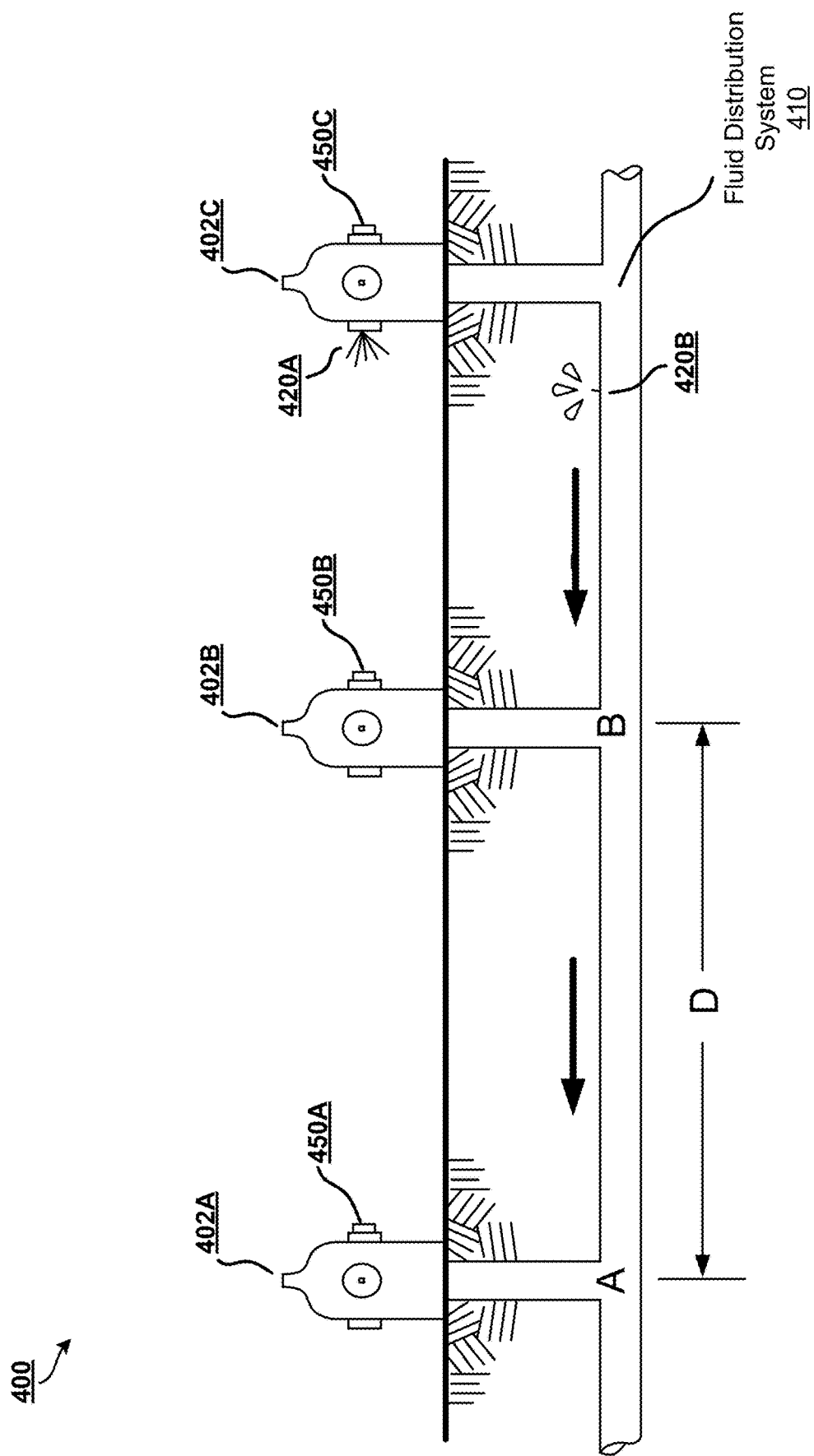
FIG. 4 illustrates a diagram of a fluid distribution system with computing nodes attached to components of the fluid distribution system for collecting and analyzing acoustic data for leak detection according to examples of the present disclosure.

FIG. 4 illustrates diagram 400 of a fluid distribution system 410 with computing nodes 450A-4500 (also referred to herein generally as computing nodes 450) for collecting and analyzing acoustic data within the fluid distribution system according to examples of the present disclosure. The fluid distribution system 410 may comprise pipes and other components (e.g., valves, couplings, fittings, meters, hydrants, etc.) used to carry fluids (e.g., water, gas, etc.) such as to customer locations. According to various aspects of the present disclosure, computing nodes 450 may be attached to the fire hydrants 402A-4020 (also referred to herein generally as fire hydrants 402). In some aspects, computing nodes 450 may be attached to each hydrant 402 while other aspects may include attachment with about every other one of the hydrants 402. In FIG. 4, for example, three adjacent fire hydrants 402A-C are shown, connected to a pipe of the fluid distribution system 410 for detecting a noise, such as noise source 420A or leak 420B. Because of the nature of a water leak, such as leak 420B, acoustic signals or vibration signals can be detected on the components (e.g., pipes, fire hydrants 402, etc.) of the fluid distribution system 410. Particularly, computing nodes 450 may be mounted on the pipes themselves or may be mounted on or within the hydrants 402. Optionally, when two leak detectors, adjacent on the fluid distribution system 410 such as computing nodes 450 mounted on hydrants 402 nearest to the leak 420B, are able to pick up acoustic signals with sufficient strength, the signals may be used to detect the presence and location of a leak. Alternatively, a computing node 450 may be located in a meter, in another communication device, as a stand-alone unit, or in any other piece of utility equipment that interfaces with the fluid distribution system 410.

FIG. 5A illustrates a flow diagram of a method 500A to analyze data collected within a fluid distribution system and implement a correlation schedule based on a selection of frequency sub-bands according to examples of the present disclosure. The method 500A may be executed by a computing system or a computing device such as computing host 120 of FIG. 1. The method 500A may also be stored as instructions on a non-transitory computer-readable storage medium such as computer-readable storage medium 330 of FIG. 3 that, when executed by a processing resource (e.g., processing resource 122 of FIG. 1 and/or processing resource 322 of FIG. 3), cause the processing resource to perform the method 500A.

At block 502, the method 500A begins and comprises receiving data for a distribution pipe network for each pipe segment. A pipe segment may generally be referred two as a length of pipe between two computing nodes, such as computing nodes 150 of FIG. 1, computing node 250 of FIG. 2, and/or computing nodes 450 of FIG. 4. An exemplary pipe segment may be illustrated in FIG. 4 as the pipe segment between points A and B. According to some aspects, the data may be manually entered by a technician or another user of the system. According to other aspects, these values may be automatically populated by the computing host as known information for a pipe segment as stored in a table. According to other aspects, these values may be automatically calculated. The pipe segment criteria may include pipe characteristics and a length of the pipe segment (e.g., a distance D between computing nodes 450A and 450B, as shown in FIG. 4). The pipe characteristics may comprise a pipe material, pipe diameter, wall thickness, geometry, and the like.

Next, at block 504, the method 500A comprises determining the characteristic frequency range for each pipe segment based on pipe material and geometry. For example, a pipe segment is a length of pipe between two computing nodes and may comprise a certain known material (e.g. steel, ductile iron, cast iron, asbestos cement, and plastic) and geometry. According to some aspects, the system may look into the attributes of acoustic propagation and identify the coherent frequency bands. Further, according to some aspects, the propagation of acoustic waves in distribution pipes may be affected by several factors that are accounted for in the system, such as pipe material, wall thickness, diameter, length of the segment, and soil composition. Based on historical data, the coherent frequency bands corresponding to certain pipe material and geometry are known, e.g., diameter, wall thickness, length, and elastic properties.

To determine the characteristic frequency range for each pipe segment at block 504, the method may comprise determining how much energy is expected in a certain sub-band schema. According to some aspects, determining of the characteristic frequency range may comprise calculating the coherent energy of signals, and displaying the frequency range in a graphical form. According to some aspects, to calculate the coherent energy of signals, Bartlett's method (also known as the method of averaged periodograms), may be used. According to some aspects, Welch's method (an approach to spectral density estimation), or other known methods in the art, may be used to calculate coherence. Examples of graphs of coherent energy of signals that propagate between two computing nodes are illustrated in FIGS. 6A and 6B.

Figure 6A:
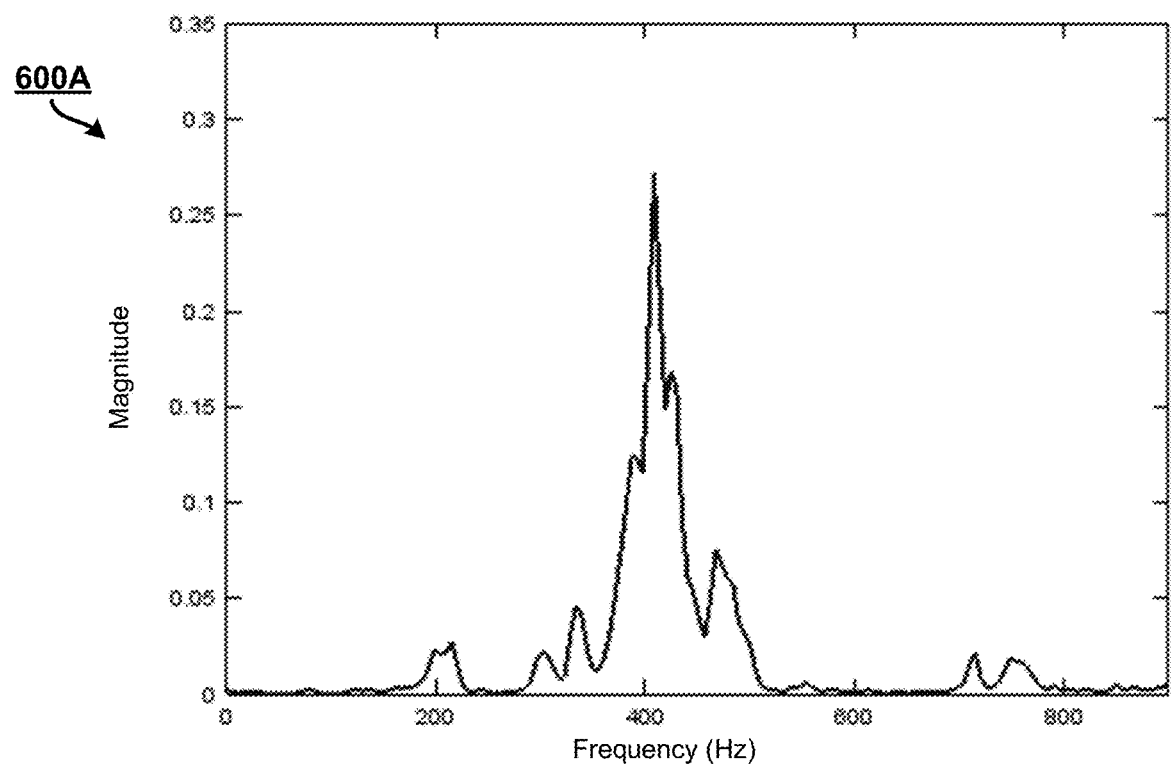
FIGS. 6A-6B illustrate graphs of data relating to coherent energy of signals that propagate between two computing nodes within a fluid distribution system according to examples of the present disclosure.
Figure 6B:
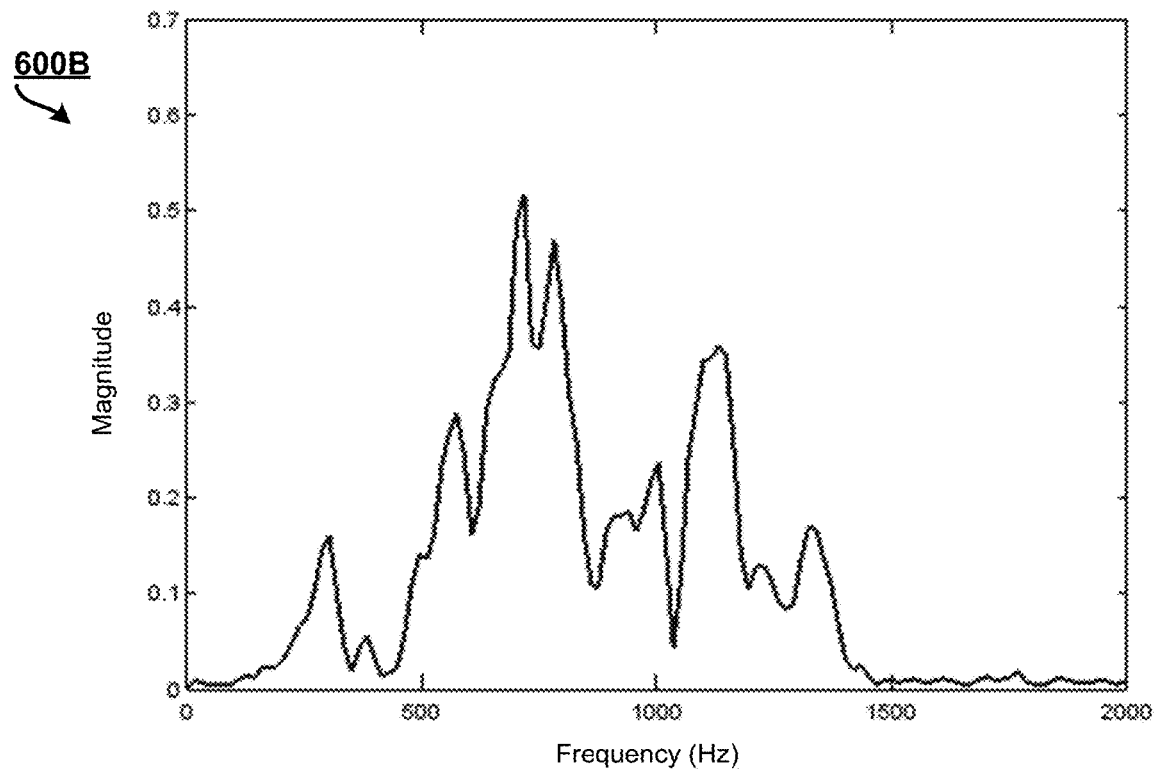

FIGS. 6A, 6B illustrate graphs 600A, 600B, respectively, of data relating to coherent energy of signals that propagate between two computing nodes, such as computing nodes 150 of FIG. 1, computing node 250 of FIG. 2, and/or computing nodes 450 of FIG. 4, within a fluid distribution system according to examples of the present disclosure. According to an exemplary aspect, graphs 600A/600B each display where energy propagates from a leak (e.g. such as leak 420B) between two sensors. For example, FIG. 6A illustrates graph 600A which illustrates coherent energy of a leak from a pipe segment comprising a ductile iron ("DI") pipe, with a diameter of 8 inches and a length of 811 feet. As another example, FIG. 6B illustrates graph 600B which illustrates coherent energy of a leak from a pipe segment comprising a cast iron ("CI") pipe, with a diameter of 8 inches and a length of 330 feet.

According to some aspects, the coherence function represents how much of the energy in each frequency bin propagates to both sensors. When coherence is low (e.g., close to zero) than the specific frequency range may not be present on both locations. When coherence is high, the signals in this frequency range reach both sensors. Coherence is a useful metric to identify which frequency bands are propagating acoustic signals better than others in a given fluid distribution system. Thus, in the example shown in FIG. 6A, the approximate frequency range of 300 Hz to 500 Hz reaches both sensors. In the example shown in FIG. 6B, the approximate frequency range of 200 Hz to 1400 Hz reaches both sensors.

According to some aspects, coherence may be calculated, and is defined by the following equation:

$$C_{oh}(f) = \frac{|C_{xy}(f)|^2}{A_{xx}(f)A_{yy}(f)}$$

Where $C_{oh}$ is coherence, $C_{xy}$ is the cross-spectral-density (CSD) or cross-spectrum, $|C_{xy}(f)|$ is the magnitude of CSD, and $A_{xx}, A_{yy}$ are power spectral density (PSD), or auto spectrum, estimates. The auto-spectrum estimates ($A_{xx}, A_{yy}$) may be calculated using method known in the art, such as Bartlett's or Welch's method of averaging periodograms. The periodogram is the magnitude of the discrete Fourier transform (DFT) of a portion of the signal (a frame), and may be defined the following equation:

$$A_{xx} = \sum \frac{DFT(x(k)^2)}{N}$$

where k is the frequency bin index, and N is the number of frames. According to some aspects, the cross-spectrum ($C_{xy}$) may be calculated as an average of the product of the DFTs of the x and y for each frame, and may be defined the following equation:

$$C_{xy} = \sum \frac{DFT(x(k)) * conj(DFT(y(k)))}{N},$$

which is based on a cross-correlation theorem known in the art, where x is the signal recorded by a first sensor, y is the signal recorded by a second sensor, and k is the index of a frequency bin. Further, the frequency corresponding to bin k may be calculated with the following equation:

$$f(k) = \frac{k}{DFT\_SIZE} * FS$$

Where FS is the sampling frequency and DFT_SIZE is the number of frequency bins used by DFT. According to some aspects, the cross-correlation between two signals is equal to the product of a DFT of one signal multiplied by a complex conjugate of a DFT of another signal.

Referring back to FIG. 5A, after a characteristic frequency range for each pipe segment is determined at block 504, next, at block 506, the method 500A comprises decomposing frequency range into multiple frequency sub-bands. According to some aspects, the system may take a signal of size Q and a given frequency bandwidth BW, and break it down to multiple sub-bands to create N signals of smaller size with a bandwidth of BW/N and a size of Q/N. Thus, after N signals are created, there would be multiple signals of smaller size, yet the total size of the signal would remain the same. For example, a signal of 10 k in size with a bandwidth of 2 kHz, could be decomposed into two signals of 5 k, each with a bandwidth of 1 Khz; thus, the total size would remain the same. Examples of decomposing signals into multiple frequency sub-bands is illustrated in FIG. 7.

Figure 7:
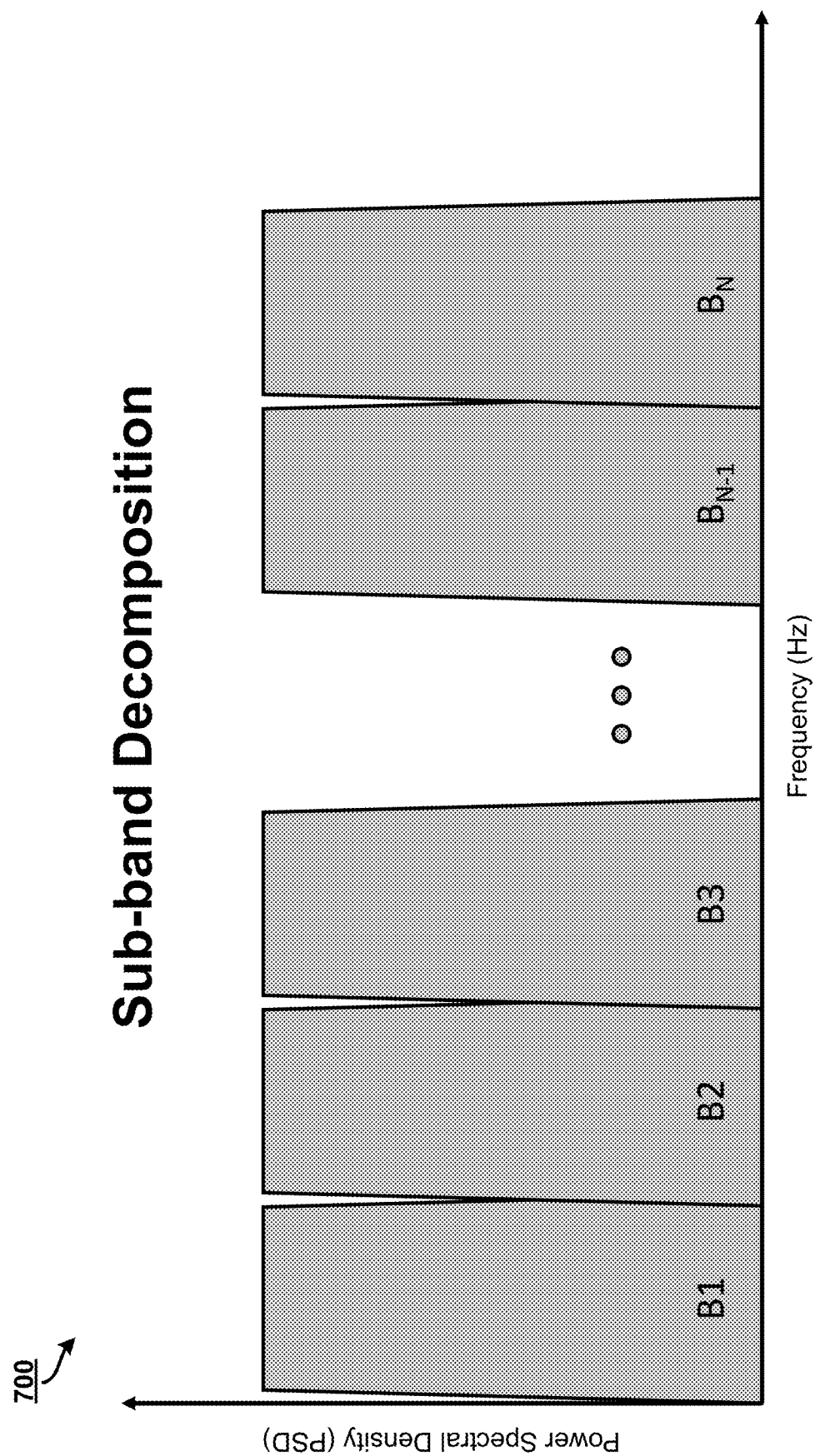
FIG. 7 illustrates a graph of data of decomposing a signal into multiple frequency sub-bands relating to techniques for analyzing data within a fluid distribution system according to examples of the present disclosure.

FIG. 7 illustrates graph 700 of frequency sub-bands according to examples of the present disclosure. In particular, FIG. 7 illustrates graph 700 of breaking down an exemplary frequency range, as discussed for block 504, above, into a number of frequency sub-bands (e.g., B1, B2, B3, $B_{N-1}$, $B_N$, etc.) as discussed for block 506, above. According to some aspects, once the decomposition has been performed into the frequency sub-bands, the system may determine which signals are more important than others for leak detection performance. One aspect for this system is determining how to select those more important bands and transmit those bands more frequently than others. This type of technique may be more commonly known in the art as "traffic shaping." According to aspects described herein, the system may prioritize those sub-bands that are more sensitive to leaks for a given pipe network. The "traffic shaping" for leak sensitivity in a given pipe network is further described below with regards to blocks 508-514 of method 500A in regards to implementing a correlation schedule.

Referring back to FIG. 5A, after decomposing frequency range into multiple frequency sub-bands is performed at block 506, next, at block 508, the method 500A comprises building a leak sensitivity model by aggregating data from every pipe segment of the distribution pipe network into corresponding frequency sub-bands. An example of a leak sensitivity model based on a distribution of coherent energy into frequency sub-bands is illustrated in FIG. 8.

Figure 8:
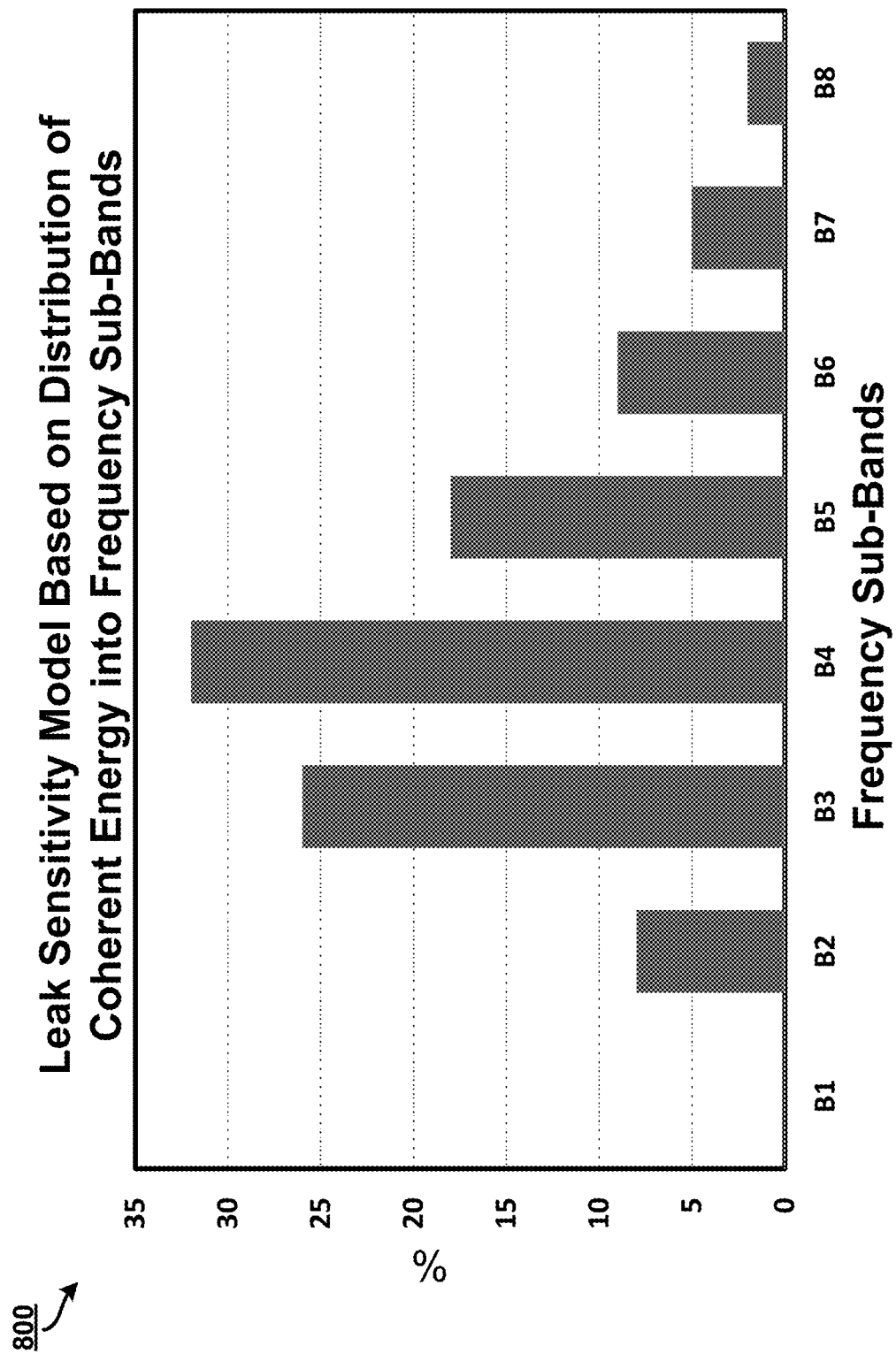
FIG. 8 illustrates a graph of data of a leak sensitivity model based on distribution of coherent energy into frequency sub-bands within a fluid distribution system according to examples of the present disclosure.

FIG. 8 illustrates graph 800 of data of decomposing a signal into multiple frequency sub-bands relating to techniques for analyzing data within a fluid distribution system according to examples of the present disclosure. In particular, FIG. 8 illustrates graph 800 of an exemplary leak sensitivity model based on a distribution of coherent energy into frequency sub-bands, as discussed for block 508, above. According to some aspects, for a given pipe distribution network, the probable coherent bands for each segment may be estimated. Further, the information may be aggregated from all segments into a distribution of coherent energy as shown in graph 800. For example, as shown in FIG. 8, frequency bin B3 occurs slightly greater than 25%, therefore that particular frequency range of bin B3 may be implemented 25% of the time in a correlation schedule. Further, for example, frequency bin B7 occurs approximately 5% of the time, therefore bin B7 may be implemented about 5% of the time in a correlation schedule.

Referring back to FIG. 5A, after a leak sensitivity model of corresponding frequency sub-bands is built by aggregating data from every pipe segment of the specific given distribution pipe network at block 508, the method 500A advances to block 510, which comprises determining a correlation schedule to maximize the acoustic propagation detection system's sensitivity to leaks. According to some aspects, each given distribution network would have a different distribution of coherent energy and would depend on the material and the geometry of the pipes used in the system. Thus, in order to maximize the acoustic propagation detection system's sensitivity of a given pipe network, a schedule may be created that sends the important frequency bands more frequently as they are more likely to catch leaks in a given pipe network; however, every site is different because they may use different type of material and size of pipe in the network. Thus each pipe network would provide different frequency ranges that would be excited by a leak.

According to an exemplary aspect, a cast iron ("CI") pipe network with a 6" diameter may excite a middle frequency range between 200 to 800 Hertz ("Hz"). According to some aspects, leaks on service lines may excite the high frequency bands range of 500 to 1200 Hz. According to some aspects, an asbestos cement ("AC") pipe network with a 12" diameter may excite low frequency range 50 to 250 Hz. According to some aspects, a polyvinyl chloride ("PVC") pipe network may excite a very low frequency range 10 to 200 Hz. Tuning the acoustic propagation detection system by determining a correlation schedule in this step (block 510) would benefit the system overall with either faster response times and/or provide a lower data footprint. An example of a correlation schedule utilized to maximize the acoustic propagation detection system's sensitivity to leaks is illustrated in FIG. 9.

FIG. 9 illustrates a table 900 of a correlation schedule within a fluid distribution system according to examples of the present disclosure. In particular, FIG. 9 illustrates table 900 of an exemplary correlation schedule/schema that sends the more important frequency bands (e.g. those bands that more likely to be excited during a leak event) more frequently, and the schedule may be implemented over a 28-day time period and repeated. According to some aspects, the correlation schedule may be updated based on new acoustic data and an updated frequency range as further discussed herein at block 514. According to some aspects, the correlation schedule may be updated at any point during execution of the 28-day cycle. Further, according to some aspects, the cycle length may be of a different period (e.g. 15-days, 30-days, 45-days, etc.).

According to an exemplary aspect, as shown in FIG. 9, overlapping and adjacent frequency sub-bands, e.g. bins B3 and B4, may be combined and sent (B3-B4). According to further aspects, some frequency sub-bands which are not overlapping may be combined because they are so infrequently needed. For example, bin B1 and bin B8 may be combined (not shown) and sent less frequently than other combinations of bins. According to some aspects, the combinations may be sent in powers of two, or individually. In some aspects, the frequency bins may be equal in size, or in some aspects they may not be equal in size.

Referring back to FIG. 5A, after a correlation schedule to maximize the system's sensitivity to leaks is determined at block 510, next, at block 512, the method 500A comprises implementing the correlation schedule based on a selection of sub-bands. According to some aspects, block 512 of method 500A may be implemented by each of the computing nodes (e.g. computing nodes 150 of FIG. 1, computing node 250 of FIG. 2, and/or computing nodes 450 of FIG. 4), by a computing host (e.g. computing host 120 of FIG. 1 or computing host 320 of FIG. 3), or on the acoustic propagation detection system being utilized to detect the leaks in the given pipe distribution network (e.g. diagram 400 in FIG. 4).

According to some aspects, implementing a correlation schedule may comprise of periodically collecting acoustic data from the plurality of nodes for the given distribution pipe network utilizing the sub-band information based on the correlation schedule. Additional details of the implementing the correlation schedule step (block 512) specifically on each computing node is illustrated in the method 500B of FIG. 5B.

After the correlation schedule has been implemented at block 512 as described above, method 500A advances to block 514, which comprises updating the frequency range for each pipe segment utilizing new field data from the plurality of computing nodes, such as computing nodes 150 of FIG. 1, computing node 250 of FIG. 2, and/or computing nodes 450 of FIG. 4. According to an exemplary aspect, as shown in FIG. 5A, as the updated frequency range is received, the process of method 500A is continuously repeated with blocks 508-514, where the updated frequency range from block 514 is used to build an updated leak sensitivity model at block 508 by aggregating the newly acquired field data from block 514 with the historical data utilized initially at block 508.

Additional processes also may be included, and it should be understood that the processes depicted in FIG. 5A represent illustrations, and that other processes may be added or existing processes may be removed, modified, or rearranged without departing from the scope and spirit of the present disclosure.

Figure 5B:
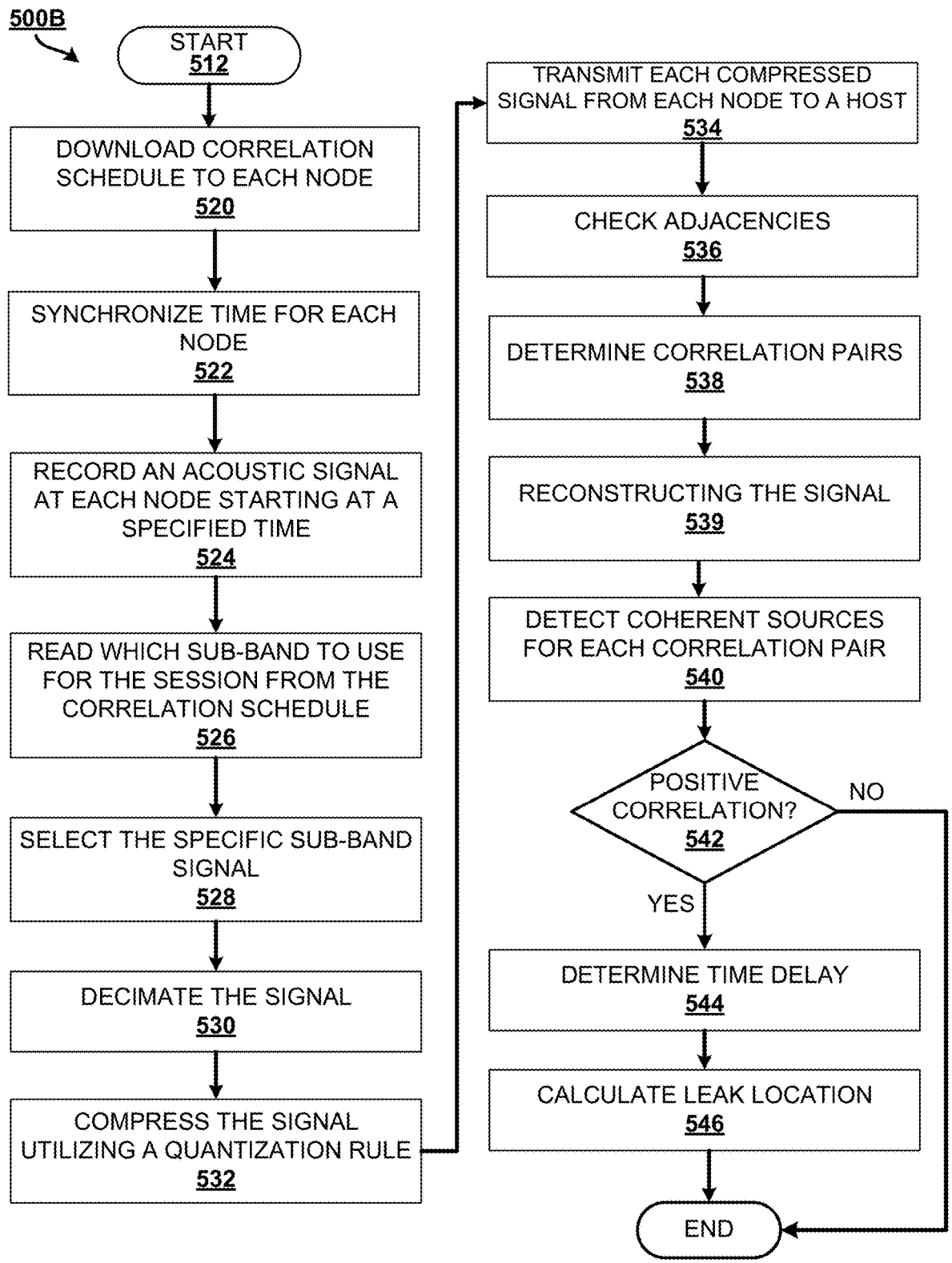

FIG. 5B illustrates a flow diagram of a method 500B to implement the correlation schedule step (block 512) of method 500A of FIG. 5A according to examples of the present disclosure. The method 500B may be executed by a computing node such as computing nodes 150 of FIG. 1, computing node 250 of FIG. 2, and/or computing nodes 450 of FIG. 4, or other suitable computing device. The method 500B may also be stored as instructions on a non-transitory computer-readable storage medium such as computer-readable storage medium 330 of FIG. 3 that, when executed by a processing resource (e.g., processing resource 122 of FIG. 1 and/or processing resource 322 of FIG. 3), cause the processing resource to perform the method 500B. The process flow of method 500B is described herein as being performed by a computing node, which should be understood to be any suitable node or computing device as described herein.

At block 520, the method 500B begins and comprises initialization for each computing node by downloading the correlation schedule to each node from a source, such as a computing host. According to some aspects the initialization step (520) may comprise downloading a calendar schedule to describe a recurring collection pattern at each node. Once the schedule is downloaded, the node may operate autonomously until the schedule is changed. According to some aspects, a node may be notified of a schedule change through a push notification, or the like, or each node may be configured to periodically poll a host to determine a schedule change. According to some aspects the initialization step 520 may include triggering a new collection schedule and sending the collection parameters prior to implementing the collection schedule. The parameters for the next collection may be sent at the end of the previous collection to daisy-chain the sequence of operation.

The method 500B continues to block 714, at which point a time synchronization is performed at each node. A local real-time-clock ("RTC") of the node may be synchronized with a reference time. According to some aspects, a local GPS receiver at each node may be used to sync the local time with the more accurate time of the GPS satellites. According to some aspects, a network beacon may be used to broadcast a time message within a specified time window. According to some aspects, each node may request a time sync from a network time server, e.g. a computing host, a remote and/or on-board GPS receiver, or other suitable device. The node clock may be synchronized to the reference time within a short time before acquisition. According to some aspects, the difference between the node clock and the reference time should not exceed ±10 milliseconds at the time of acquisition to ensure accurate location. According to some aspects, all nodes used to detect leaks may start acquiring data at the same time. In some aspects, it may be important that during acquisition the sampling frequency in all the nodes be substantially the same.

The method 500B continues and each node of the given pipe network records an acoustic signal starting at a specified time (block 524). According to some aspects, each node may start collecting at precisely the same acquisition time. According to some aspects, a maximum sampling rate may be used, e.g. 8 kHz.

The method 500B continues to block 526, where each node reads which sub-band to use for the data acquisition session from the correlation schedule/schema. The data acquisition session may include reading which sub-band will be processed and transmitted with the particular session being executed. According to some aspects, each node must use the same sub-band for the particular session. At block 528, each node may select the specific sub-band signal. After the specific sub-band signal is selected at block 528, each node may decimate the signal at block 530. The extraction and decimation of the specific sub-band signal (blocks 528 and 530) may comprise one of several different methodologies, of which, two methodologies are further described in the subsequent paragraphs.

According to some aspects, one methodology for the selection of the specific sub-band (block 528) and decimation of the specific signal (block 530) may comprise decomposing the signal into several symmetric sub-bands and select only the specified sub-band for the particular session. Symmetric sub-band decomposition may comprise breaking down the signal into two bands utilizing a low-pass filter to extract the lower frequency range, and a high-pass filter to extract the upper frequency range, resulting in two smaller halved signals, one including the low frequency range, while the other including the high frequency range. After the signal is split into two signals, each signal may be decimated by a factor of 2 (take every other sample) to reduce the file size. According to some aspects, due to smaller bandwidth, the information can be represented with a smaller sampling rate, therefore decimation may not cause loss of information. According to some aspects, this process of decomposition may be applied recursively to decompose the signal into multiple sub-bands, where the number sub-bands produced is a power of 2. For example, after decimation of each signal, those two signals may be each divided again by the same process splitting the original signal into now four signals. The process may continue to break down each resulting signal in half until a predetermined sized output sub-band is accomplished from the sub-band decomposition process.

According to an exemplary aspect of symmetric sub-band decomposition, a signal with a sampling rate of 8 kHz may be decomposed into 8 bands. The maximum representable frequency range is half the sampling frequency, thus 4 kHz. After the sub-band decomposition the original signal will be decomposed into 8 sub-bands of 500 Hz each. Subsequent decimation, the selected sub-band of 500 Hz may be encoded with a 1 kHz sampling rate (instead of the original 8 kHz), which may reduce the file size by a factor of 8. An example of symmetric sub-band decomposition is illustrated in FIG. 10.

Figure 10:
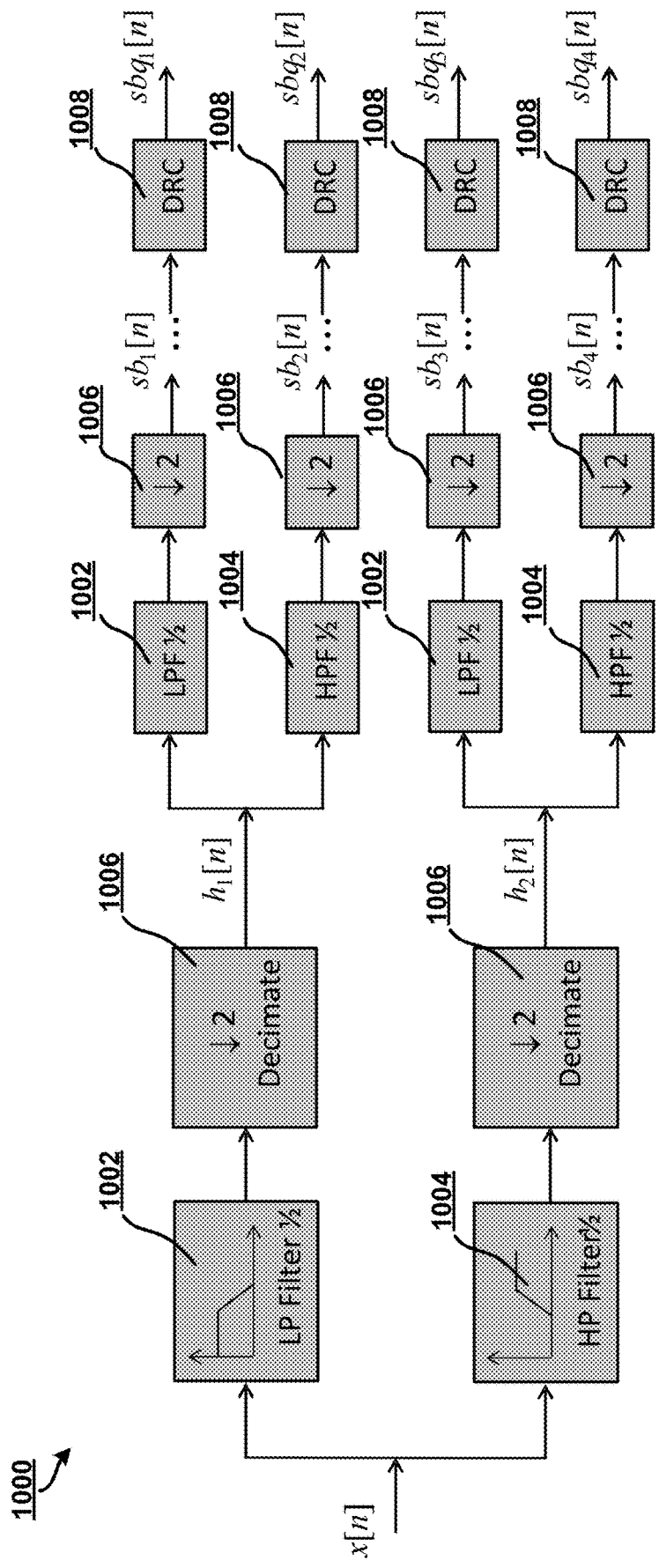
FIG. 10 is a block diagram of symmetric sub-band decomposition utilizing filtering and decimation of a signal within a fluid distribution system according to examples of the present disclosure.

FIG. 10 illustrates a block diagram of symmetric sub-band decomposition utilizing filtering and decimation of a signal within a fluid distribution system according to examples of the present disclosure. The filtering of a signal (x[n]) and splitting into two signals may be accomplished through utilizing a low pass filter 1002 and a high pass filter 1004. After the signal (x[n]) is filtered and split into two signals ($h_1[n]$, $h_2[n]$), each signal is then decimated by a factor of 2 at block 1006. The use of the low-pass filter/high-pass filter and decimation may be repeated to each signal to create four signals ($sb_1[n]$, $sb_2[n]$, $sb_3[n]$, $sb_4[n]$). According so some aspects, the process of filtering and decimating each signal may be repeated into any number signals by a power of 2. According to some aspects, the filtering and decimation techniques of FIG. 10 may use any known method in the art.

According to some aspects, another methodology for the selection of the specific sub-band (block 528) and decimation of the specific signal (block 530) may comprise applying a pass-band filter to retain the desired energy in the specific sub-band, and apply frequency shifting, filtering, and decimation of the signal. An example of frequency sub-band selection utilizing frequency shifting, filtering, and decimation of a signal is illustrated in FIGS. 11A and 11B.

Figure 11A:
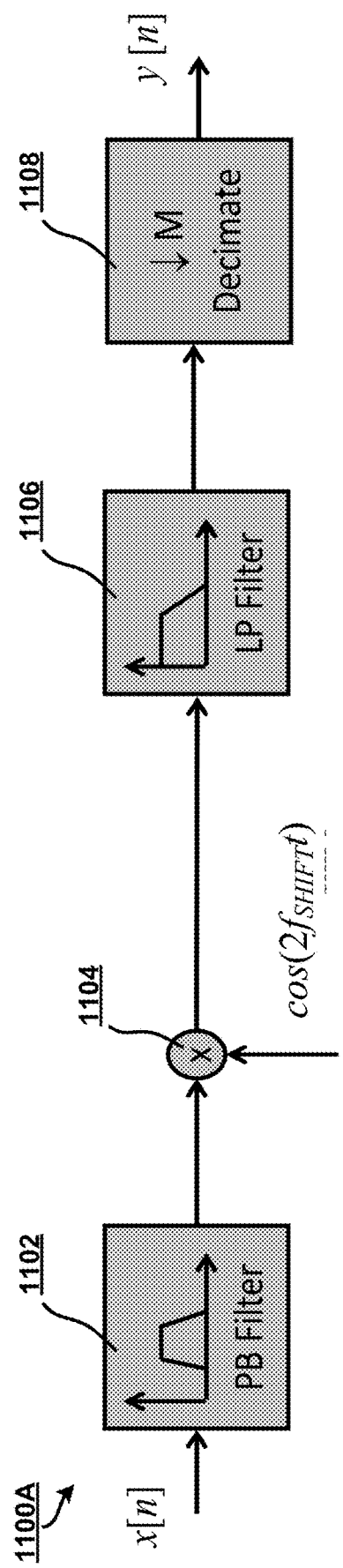
FIG. 11A illustrates a block diagram of frequency sub-band selection utilizing frequency shifting, filtering, and decimation of a signal within a fluid distribution system according to examples of the present disclosure.
Figure 11B:
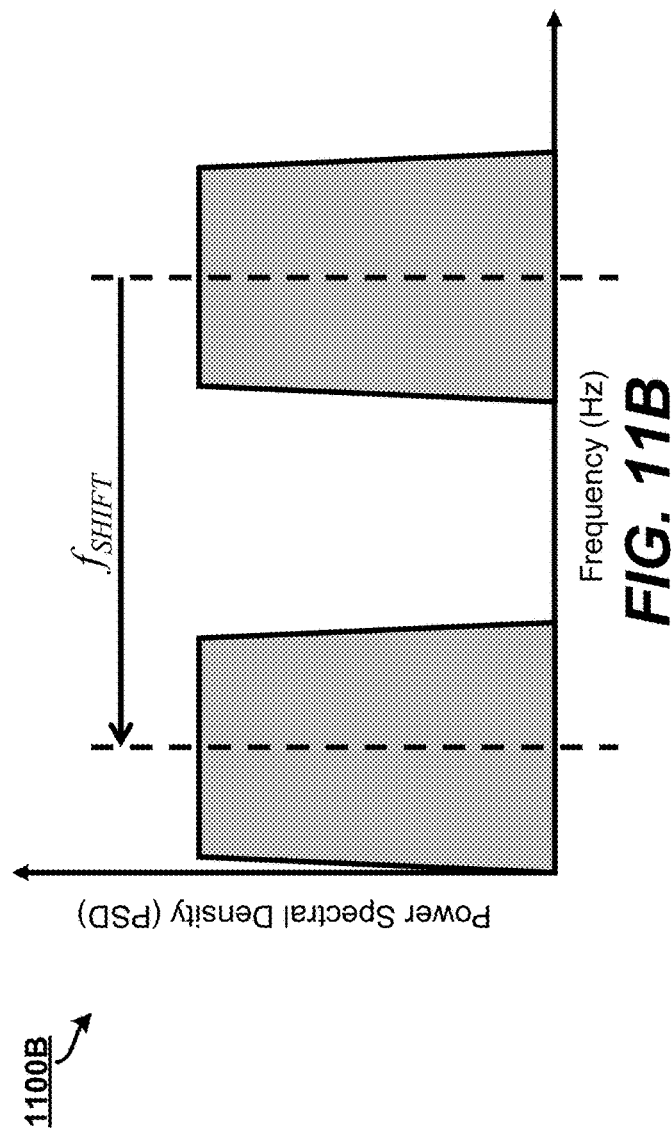
FIG. 11B illustrates a graph of data utilizing frequency shifting for a signal within a fluid distribution system according to examples of the present disclosure.

FIG. 11A illustrates a block diagram 1100A of frequency sub-band selection utilizing frequency shifting, filtering, and decimation of a signal within a fluid distribution system, and FIG. 11B illustrates a graph 1100B of frequency shifting of a signal within a fluid distribution system, according to examples of the present disclosure. In particular, the signal (x[n]) is sent through a pass-band filter 1102 to extract relevant information, multiplied with a tone 1104 to create two mirrored spectral images shifted with the frequency of the tone (FIG. 11B), sent through a low-pass filter 1106, and then decimated 1108 to reduce the size of the signal (y[n]).

Referring back to FIG. 5B, after the selection of the specific sub-band (block 528) and decimation of the specific signal (block 530), next, at block 532, the method 500B comprises compressing the signal utilizing quantization. With quantization, the data may be filtered and compressed (such as by "clipping") without losing necessary frequency and phase information for analysis. An example of clipping is 1-bit compression, where the file size may be reduced by a factor of 16 (e.g., 16-bit to 1-bit). This compression preserves the phase and detects and locates acoustic sources on distribution networks. For example, if (Xin>=0), then Xout=1, or if (Xin<0), then Xout=0. An example of filtering and compressing acoustic data (such as by "clipping") without losing necessary frequency and phase information for analysis is illustrated in FIGS. 12A and 12B.

Figure 12A:
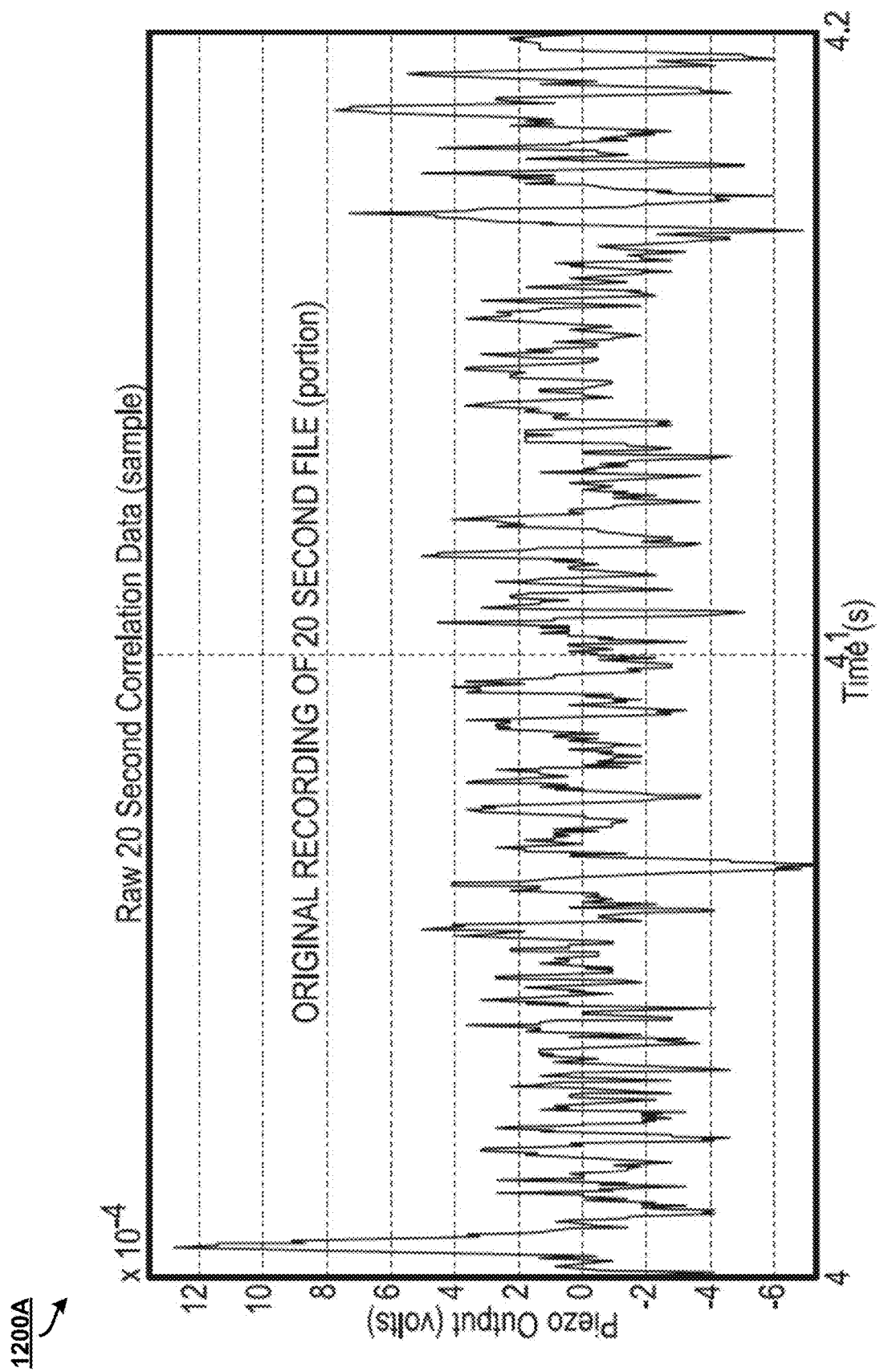
FIGS. 12A and 12B respectively illustrate graphs of raw and compressed data relating to the techniques for collecting and analyzing data within a fluid distribution system according to examples of the present disclosure.
Figure 12B:
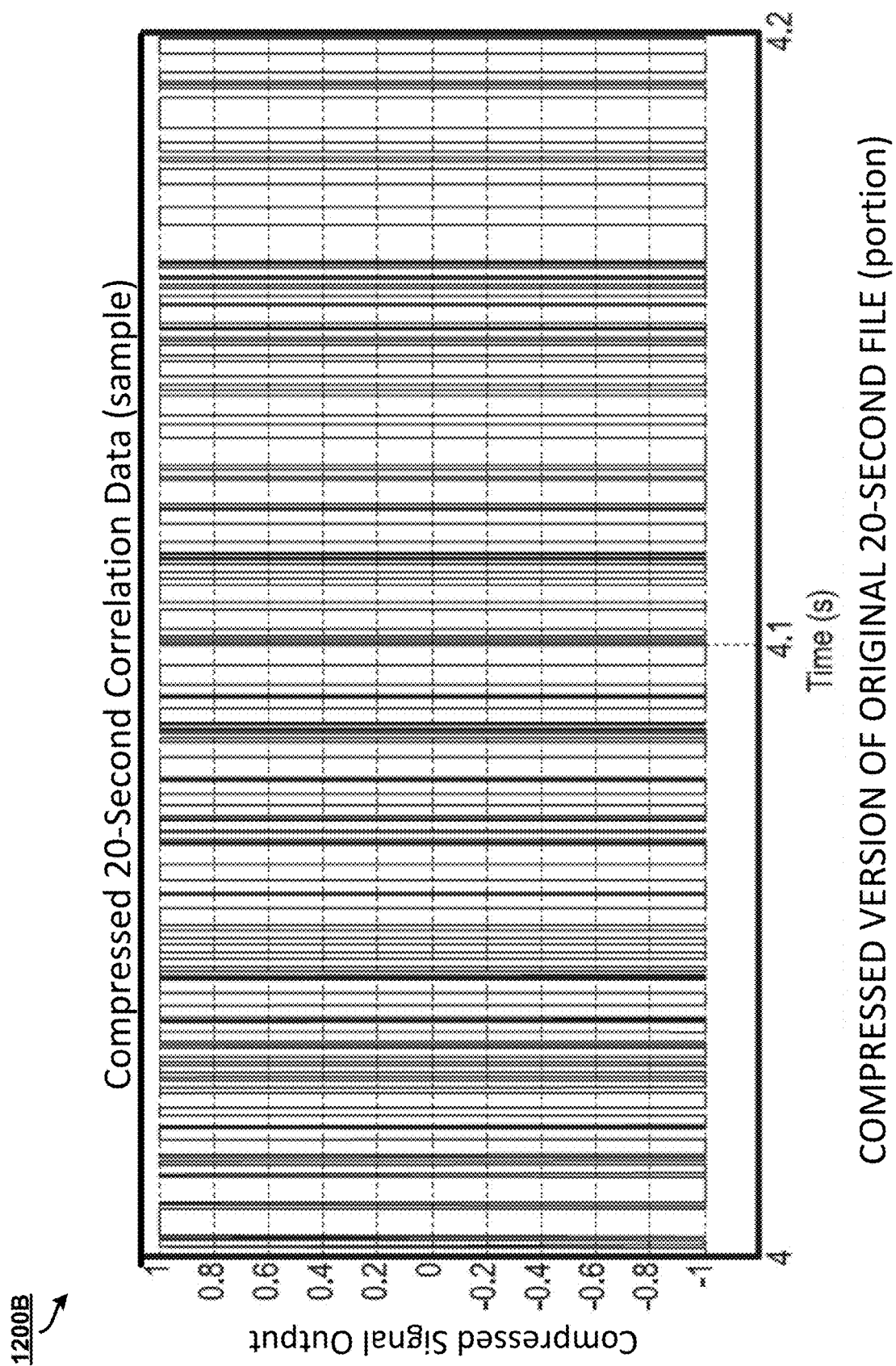

FIGS. 12A and 12B illustrate graphs 1200A and 1200B of raw and compressed data, respectively, relating to the techniques for collecting and analyzing data within a fluid distribution system according to examples of the present disclosure. As discussed herein, raw acoustic data is recorded by the nodes of a water distribution system such as for leak detection. In examples, 20 seconds of 32-bit samples at a sampling rate of 4 KHz produces 312.5 KB of raw acoustic data. This acoustic data may be produced nightly by hundreds or thousands of nodes and then sent to a computing host for analysis (correlation).

A computing node (e.g., nodes 150 of FIG. 1, computing node 250 of FIG. 2, computing nodes 450 of FIG. 4, etc.) may filter and compress (for example, "clip") the raw acoustic data of FIG. 12A before transmission to a computing host. Because the correlation analysis performed by the computing host (e.g., computing host 120 of FIG. 1 and/or computing host 320 of FIG. 3) is concerned with frequency and phase, the amplitude information in the time domain may be omitted. Therefore, the data can be filtered and compressed (such as by "clipping") without losing necessary frequency and phase information for analysis. In the example illustrated in FIG. 12A, the 32-bit value for each sample is converted to a +1 if the value is positive and −1 if the value is negative resulting in graph 1200B as illustrated in FIG. 12B. Thus each sample may be represented with one bit instead of 32 bits. For example, 312.5 KB of raw acoustic data may be reduced to approximately 9.75 KB of compressed data.

According to some aspects, other quantization methods known in the art may be used to compress the signal at block 532. According to some aspects, one quantization method that may be used is a non-linear pulse code modulation ("PCM") utilizing Standard G.711 or Standard G.726, for example. These methods compress the raw data (usually 16-bit) into fewer bits (8 or 4) using a nonlinear function. Standard G.726 uses adaptive differential pulse code modulation ("ADPCM"). According to some aspects, the adaptive mechanism of ADPCM may be modified using an optimal sub-band correlation schedule tuned to a given pipe network, as described herein.

According to some aspects, one quantization method that may be used is differential pulse code modulation ("DPCM"), or absolute pulse code modulation ("APCM"). DPCM may encode the difference between two successive samples as may be expected that local differences are small. According to some aspects, the nonlinear function of using DPCM or APCM may be aggressive (e.g., 16-bit compressed into 1-bit through clipping).

According to some aspects, filtering and compressing of the raw acoustic data occurs at the node (e.g., nodes 150 of FIG. 1, computing node 250 of FIG. 2, computing nodes 450 of FIG. 4, etc.) and, in examples, may be performed by a microcontroller and/or DSP in the node. In some embodiments, some frequency components may be removed at the node from the raw acoustic data before compression is performed.

After the selected sub-band signal is compressed at block 532, method 500B advances to block 534, which comprises transmitting each compressed signal from each node to the computing host (e.g., computing host 120 of FIG. 1 and/or computing host 320 of FIG. 3). The computing host, at block 536, may check for adjacencies based on geographic information system ("GIS") data from each node of the plurality of nodes in the given network. Further, at block 538, method 500B may comprise determining correlation pairs from the adjacencies. According to some aspects, the physical pipe network information may be generated using GIS data sourced from the customer's documentation whereas correlation adjacencies may be determined through a two-step process. First, the system automatically determines possible correlation pairs based on adjacency criteria. Second, a manual review of the automatically determined adjacencies for errors may be performed.

After correlation pairs are determined at block 538, method 500B advances to block 539, which comprises signal reconstruction. One methodology for a signal reconstruction scheme is symmetric sub-band reconstruction. With this scheme, each received sub-band is interpolated, where the sampling frequency of the signal is doubled by inserting zero samples in between the original samples, then an interpolation filter is applied. Then the interpolated signals are combined by direct summation. Since the signal was compressed at the transmitter with a nonlinear law, the inverse of this law will be applied to expand the dynamic range. Thus, a dynamic range expander ("DRE") will be applied as a first step of the signal reconstruction process. An example symmetric sub-band reconstruction scheme is illustrated in FIGS. 13-14.

Figure 13:
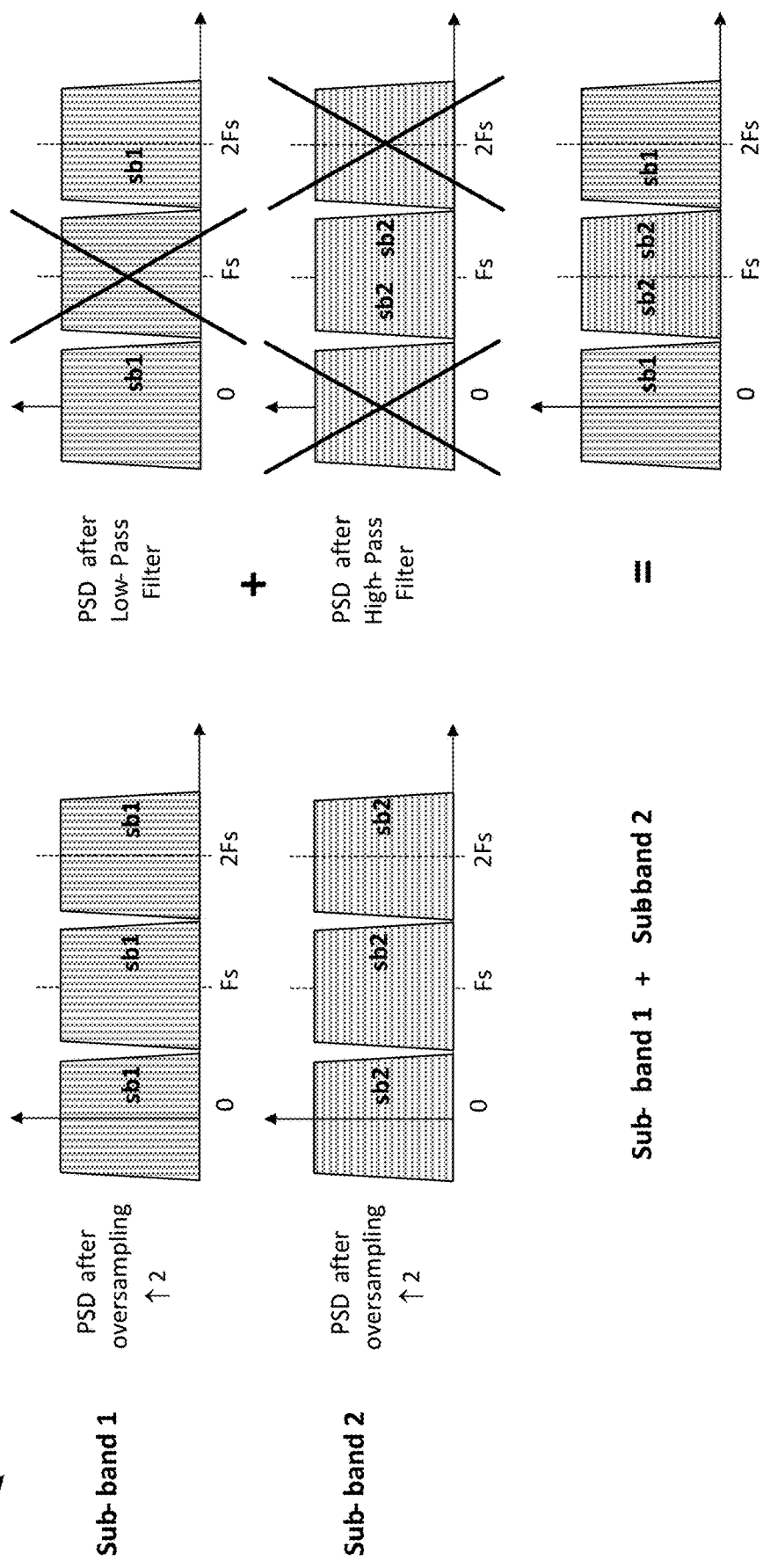
FIG. 13 illustrates a block diagram of a process of reconstructing the signal within a fluid distribution system from two distinct sub-bands signals according to examples of the present disclosure.

FIG. 13 illustrates a block diagram 1300 of signal reconstruction from two sub-bands within a fluid distribution system, according to examples of the present disclosure. In particular, a first sub-band input is passed through a low-pass interpolation filter, and a second sub-band input is passed through a high-pass interpolation filter. The resulting filtered sub-bands are then combined into the reconstructed signal. As shown in FIG. 13, the power spectral density (PSD) of the reconstructed signal includes both spectra of the input sub-bands.

Figure 14:
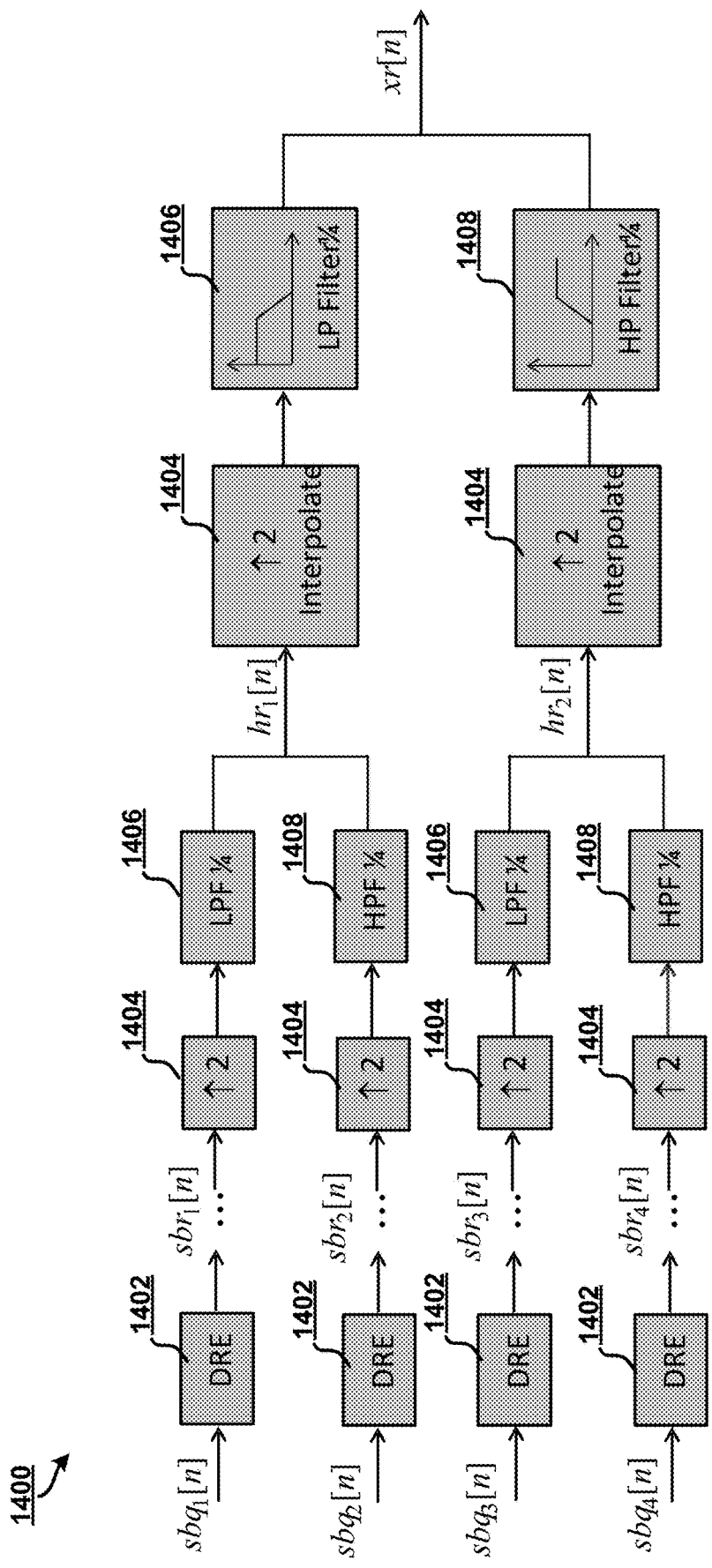
FIG. 14 is a block diagram of symmetric sub-band reconstruction utilizing interpolation and summation of a signal within a fluid distribution system according to examples of the present disclosure.

FIG. 14 illustrates a block diagram of symmetric sub-band reconstruction within a fluid distribution system according to examples of the present disclosure. The signals ($sbq_1[n]$-$sbq_4[n]$) are each passed through a DRE 1402 to expand the dynamic range. The resulting signals ($sbr_1[n]$-$sbr_4[n]$) are then passed through an interpolation filter 1404. After being interpolated, half of the signals (e.g. every odd numbered signal) are passed through a low pass filter 1406, and the other half of signals are passed through a high pass filter 1408. Every signal that went through a low pass filter is combined with a signal that went through a high pass filter by direct summation, resulting in half as many signals ($hr_1[n]$, $hr2[n]$, etc.). Some aspects of this process are illustrated in FIG. 13, which shows the reconstruction of the original power spectral density (PSD) from two sub-band signals. The use of interpolation filters and low-pass filter/high-pass filters may be repeated to the remaining signals until there is one resulting signal ($xr[n]$). According so some aspects, the process of filtering and interpolating each signal may be repeated into any number signals by a power of 2. According to some aspects, the sub-band reconstruction techniques of FIG. 14 may use any known method in the art.

Referring back to FIG. 5B, after the signal is reconstructed at block 539, method 500B advances to block 540, which comprises detecting coherent sources for each correlation pair. According to some aspects, the computing host may determine if there is a positive correlation (block 542). If there are no positive correlations, than method 500B (implementation of the correlation schedule step of block 512) terminates. However, if a positive correlation is determined at block 542, then method 500B further comprises determining a time delay (block 544) and calculating a leak location (block 546) utilizing leak detection methods for the specific acoustic propagation detection system being used. A positive correlation test is defined by the fact that the correlation function forms a peak. If the peak/rms ratio exceeds a certain threshold, this is indicative of a possible leak. The location of the correlation peak is determined by the time delay between the two received signals origination from the same source. Knowing the spacing between sensors, the time delay and the propagation speed of sound in the specific pipe one can determine accurately the location of the leak. After the leak location is calculated (block 546), method 500B terminates.

Figure 15:
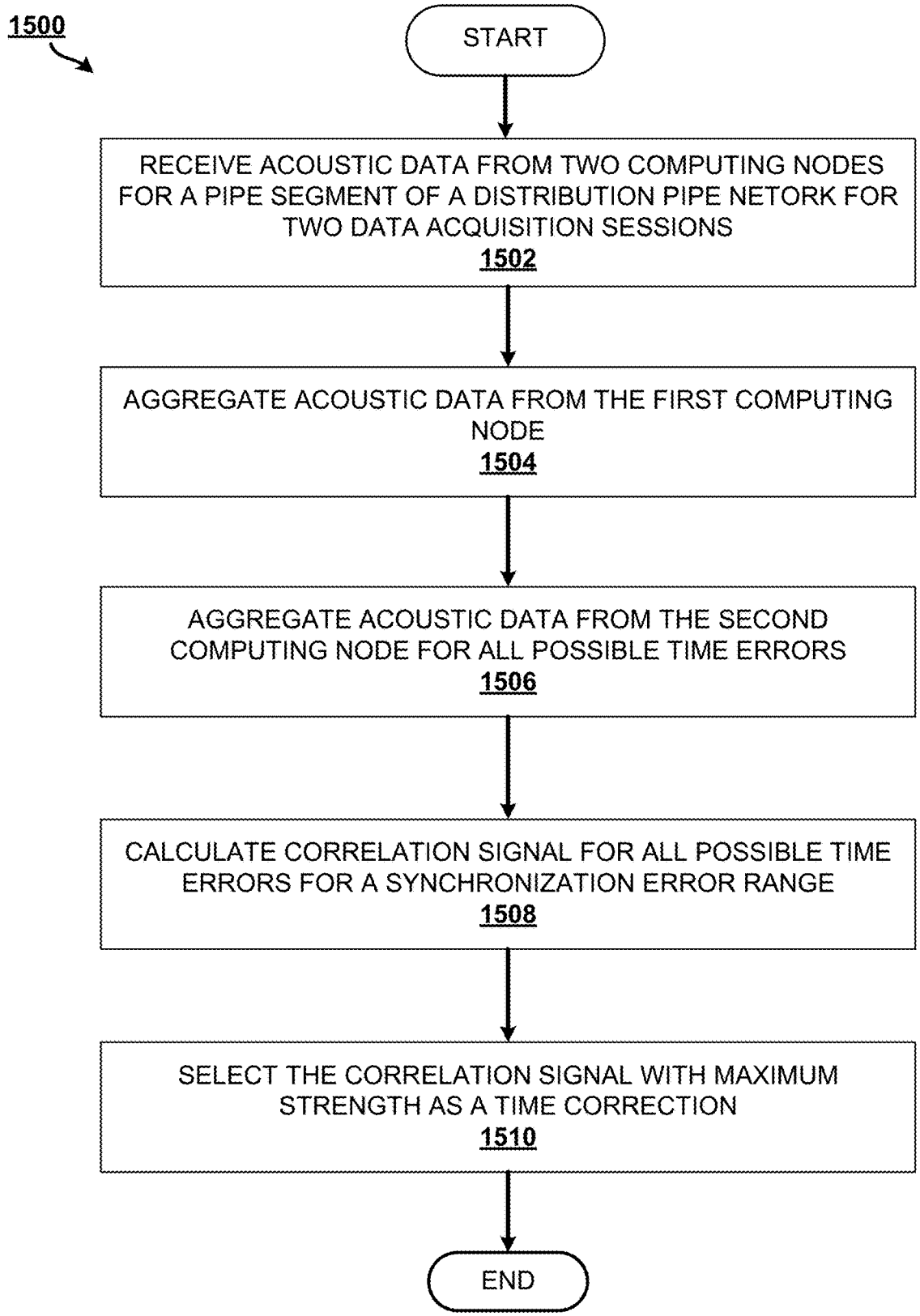
FIG. 15 illustrates a flow diagram of a method to collect and analyze data to calculate and select a correlation signal with a maximum strength as a time correction within a fluid distribution system according to examples of the present disclosure.

FIG. 15 illustrates a flow diagram of a method 1500 to aggregate multiple acoustic samples taken at distinct times utilizing a correlator for leak detection for a plurality of pipe segments of a distribution pipe network according to examples of the present disclosure. The method 1500 may be executed by a computing system or a computing device such as computing host 120 of FIG. 1. The method 1500 may also be stored as instructions on a non-transitory computer-readable storage medium such as computer-readable storage medium 330 of FIG. 3 that, when executed by a processing resource (e.g., processing resource 122 of FIG. 1 and/or processing resource 322 of FIG. 3), cause the processing resource to perform the method 1500.

At block 1502, the method 1500 begins and comprises receiving acoustic data from two computing nodes for a pipe segment of a distribution pipe network for two data acquisition sessions. According to some aspects, block 1502 may be represented as: "Session 1 (Ch1+Ch2) and Session 2 (Ch1+Ch2)," where Ch1 represents a first computing node, and Ch2 represents a second computing node.

Next, the method 1500 advances to block 1504, which comprises aggregating acoustic data from the first computing node. According to some aspects, block 1502 may be represented as: "$CH1_A$=(Session 1+Session 2)." An example of aggregating acoustic data for a computing node is illustrated in FIG. 16.

Figure 16:
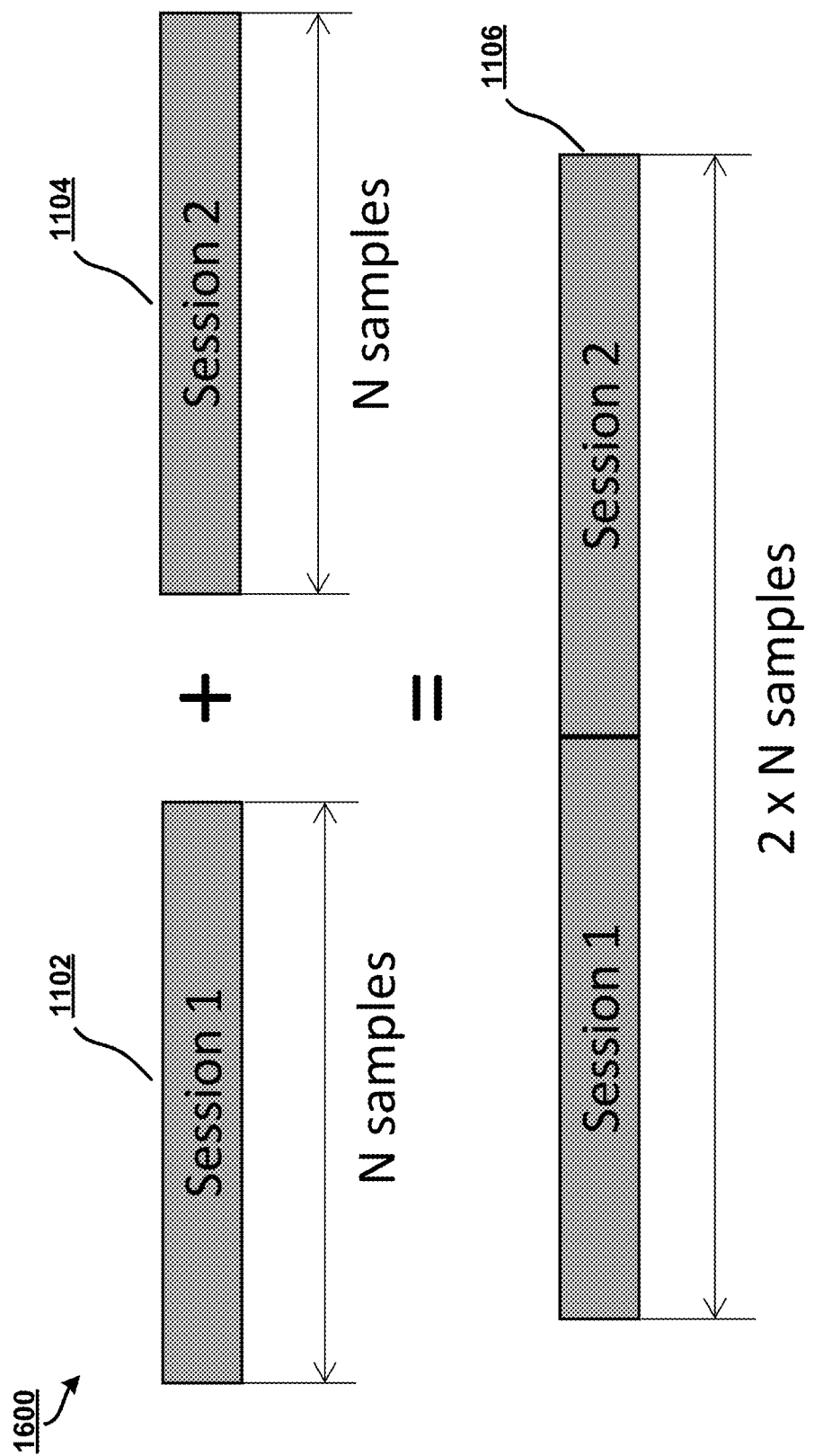
FIG. 16 illustrates a block diagram of a leak detection correlator with time aggregation within a fluid distribution system according to examples of the present disclosure.

FIG. 16 illustrates a block diagram 1600 of a leak detection correlator with time aggregation within a fluid distribution system according to examples of the present disclosure. As shown in FIG. 16, each session includes two signals between two computing nodes, and the two sessions need to be synchronized for an improved processing gain, as signal-to-noise ratio (SNR) improves with processing gain, and is defined by the following equation:

$$SNR = \alpha \sqrt{N_{SAMPLES}}$$

where $\alpha$ is a proportional width.

If each node has a near-perfect time reference (i.e. GPS) then the system can aggregate each signal from the two nodes directly. According to some aspects, near-perfect time means time error is less than 100 us. However, according to an exemplary aspect, synchronization between nodes is not near-perfect time, therefore the system needs to correct for time errors before aggregation for the second computing node (block 1506). According to some aspects, it may be expected to have errors up to 20 milliseconds; thus, according to an exemplary aspect, the synchronization error range is from −20 milliseconds to 20 milliseconds, with a sampling rate 0.1 milliseconds. After the acoustic data is aggregated from the first computing node at block 1504, the method 1500 advances to block 1506, which comprises aggregating acoustic data from the second computing node for all possible time errors (e.g. a synchronization error range). According to some aspects, block 1506 may be represented as: "$CH2_A$=(Session 1+Session 2)."

According to some aspects, a sound from a leak source may arrive at the first computing node after $dt_1$ and at the second computing node after $dt_2$. The true time difference between channel 1 and channel 2 (computing node 1 and computing node 2), $\Delta t$, may be represented by the equation:

$$\Delta t = dt_1 - dt_2.$$

For the first session, there may be a time error, $err_{T1}$. Thus, the difference between channel 1 and channel 2 for the first session, $\Delta t_1$, may be represented by the equation:

$$\Delta t_1 = dt_1 - dt_2 - err_{T1}.$$

For the second session, there may be a time error, $err_{T2}$, thus the difference between channel 1 and channel 2 for the second session, $\Delta t_t$, may be represented by the equation:

$$\Delta t_t = dt_1 - dt_2 - err_{T2}.$$

Time correction ("TimeCorr") may then be calculated by computing the difference between each time error ($err_{T1}$, and $err_{T2}$) or the difference between the differences of each channel for each session ($\Delta t_1$ and $\Delta t_2$), and may be represented by the equation:

$$TimeCorr = \Delta t_1 - \Delta t_2 = err_{T1} - err_{T2}$$

According to aspects described herein, the system may search for the best time correction (TimeCorr) by shifting channel 2 of session 2 one sample time at a time. The search may be conducted over the entire time synchronization error range (e.g. time synchronization error range of ±20 ms). According to some aspects, the sampling time may vary depending on the type of pipe material (e.g. steel, ductile iron, cast iron, asbestos cement, and plastic), and the acoustic propagation detection system used. Examples of aggregating acoustic data for the second computing node for all possible time errors are illustrated in FIGS. 17A-17C.

Figure 17A:
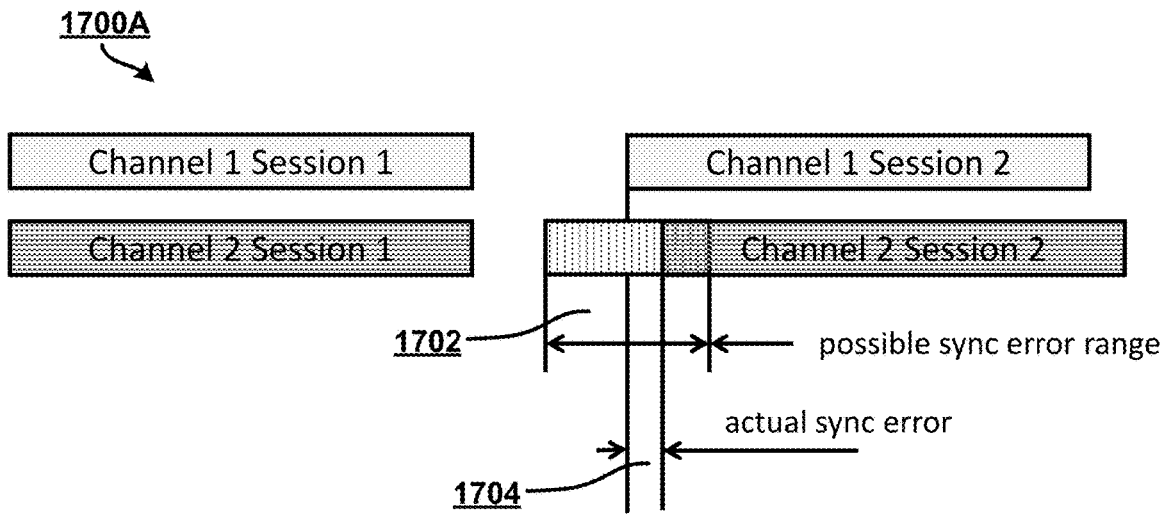
FIGS. 17A-17O illustrate block diagrams for re-synchronization between two computing nodes and two different sessions within a fluid distribution system according to examples of the present disclosure.
Figure 17B:
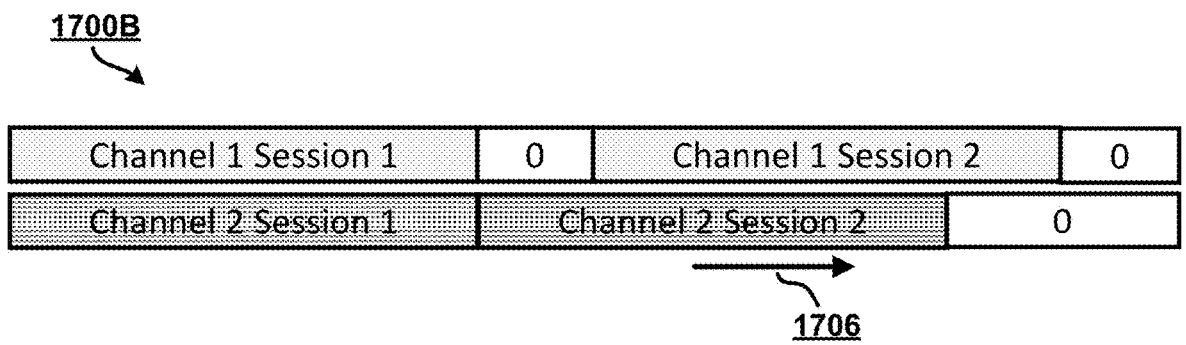
Figure 17C:
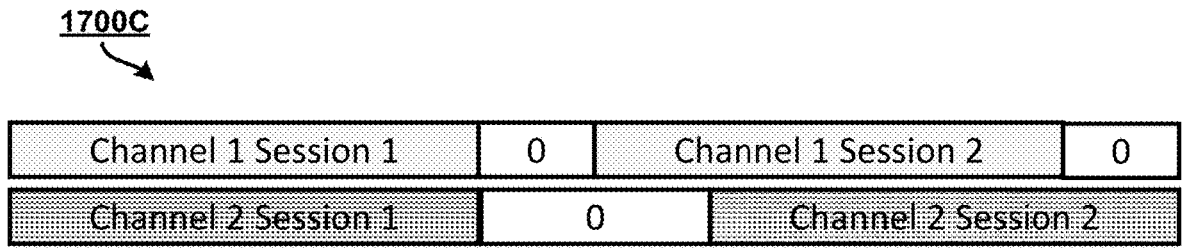

FIGS. 17A-17O illustrate block diagrams 1700A-1700C for re-synchronization between two computing nodes and two different sessions within a fluid distribution system according to examples of the present disclosure. In particular, the block diagram 1700A of FIG. 17A represents a possible sync error range 1702 and an example of the actual sync error 1704 for two sessions of data acquisition for two channels. The block diagram 1700B of FIG. 17B represents an example block diagram for two sessions of data acquisition for two channels before shifting and correlation has been implemented for the second session of channel 2 as discussed below (block 1508). The block diagram 1700C of FIG. 17C represents an example block diagram for two sessions of data acquisition for two channels after shifting and correlation have been implemented for the second session of channel 2 as discussed below (block 1508) in order to account for all possible time errors.

Referring back to FIG. 15, after the acoustic data from the second computing node for all possible time errors is aggregated at block 1506, the method 1500 advances to block 1508, which comprises calculating a plurality of correlation signals for all possible time errors (e.g., a synchronization error range) by correlating synchronized acoustic data sets from a pair of nodes to produce a corresponding correlation signal for each sample at a given sample rate. According to an exemplary embodiment, calculating the plurality of correlation signals comprises shifting the second acoustic data set from the second node one sample at a time for the synchronization error range, correlating the entire acoustic data set from the first node with the entire acoustic data set from the second node for each sample for the synchronization error range, and determining a maximum value for each correlation signal of the plurality of correlation signals.

According to some aspects, a correlation signal may be analyzed to determine the presence of a leak and provide a general estimation of where the leak is located. Correlation may occur as part of a daily analysis process, initiated by a system user request, or as part of system-wide correlation. For example, according to some aspects, leak detection may not capture all leak conditions; therefore, a periodic system-wide correlation scan may be required. The periodic system-wide correlation scan may include a host which collects all synchronized acoustic data sets from a site at a given time and analyses of all adjacency pairs. According to some aspects, an operator may request a correlation between a pair of computing nodes to confirm a leak or maintenance purpose. A single correlation pair signifies two nodes to be correlated together, and the correlation result is the data generated from analyzing a correlation signal between the correlation pair. The correlation signal is calculated by cross-correlating the synchronized data sets received from a pair of computing nodes. The cross-correlation is a similarity test between two discrete signals that can be expressed as a sliding dot-product according to the formula:

$$corr[k] = \sum_{i=1}^{L} a[i] \cdot b[i+k] \quad k = -MCD \text{ to } MCD$$

where a and b are the two discrete signals, comprised of L samples each, and corr is the computed cross-correlation signal comprised of 2MCD+1 samples. Maximum correlation domain ("MCD") is a correlation domain limit that represents the upper or lower bound of the correlation domain expressed in number of samples. To ensure a comprehensive analysis, the correlation domain shall include the maximum expected time-delay $DT_{MAX}$.

$$MCD > DT_{MAX} Fs = \left[\frac{d_{ab}}{c} Fs\right]$$

The maximum expected time-delay $DT_{MAX}$ is determined by the ratio of the distance between the nodes $d_{ab}$ to the speed of sound c in the pipe system. The resulting time shall be multiplied by the sampling frequency Fs to compute the corresponding number of samples. In some embodiments, the correlation domain limit MCD is chosen as a power of two larger than the maximum expected time-delay $DT_{MAX} Fs$.

The cross-correlation signal corr[k] at index k indicates how similar is one signal when compared to the other one shifted by k samples. If a leak occurs, it will produce an acoustic signal that shall propagate through the pipe system and excite both sensors with a similar pattern. The leak signals will reach each sensor with a certain time delay, dependent on the pipe geometry and the speed of sound in the pipe system. For a certain shift k, the two signals are expected to align and the cross-correlation shall present a significant maximum. The location of the cross-correlation maximum represents the time delay for which the two acoustic signals are best aligned. This information is essential for both leak detection and leak location purpose. It is well known that the cross-correlation function can be implemented efficiently through a frequency domain transformation by using a fast Fourier transform algorithm. In addition, certain filters and processors may be applied to sharpen the cross-correlation peak.

According to some aspects, the leak detection process may be based on detecting a peak in the cross-correlation signal. If the peak occurs at the time delay within a prescribed interval and the ratio between the peak value and the root-mean-squared ("RMS") value exceeds a detection threshold, then a point-of-interest is indicated. A point-of-interest indicates the presence of an acoustic source between two nodes which may be caused by a leak. The detection threshold is based on statistical properties of noise to discriminate a true acoustic source from background noise. In some embodiments, a six-sigma band is considered for establishing the detection threshold. The position of the strongest cross-correlation peak represents the time delay between the two acoustic signals and it can be used in conjunction with the distance between the nodes and the predicted speed of sound in the pipe system to locate the possible leak. A maximum expected time-delay is determined by the ratio of the distance between the nodes to the speed of sound. The maximum expected time-delay serves as a check to determine whether a data anomaly exists. In other words, since the distances between nodes and the speed of sound are both known, they allow calculation of an expected delay, which can be compared to the delay indicated by the correlation signal. If the delay indicated by that signal exceeds the expected delay, a data anomaly may be present.

Finally, after calculating a plurality of correlation signals for a synchronization error range by correlating synchronized acoustic data sets from a pair of nodes to produce a corresponding correlation signal for each sample at a given sample rate (block 1508), at block 1510, the method 1500 comprises selecting the correlation signal with a maximum strength as a time correction and terminates. An example of selecting the correlation signal with a maximum strength as the correct time correction is illustrated in FIG. 18.

Figure 18:
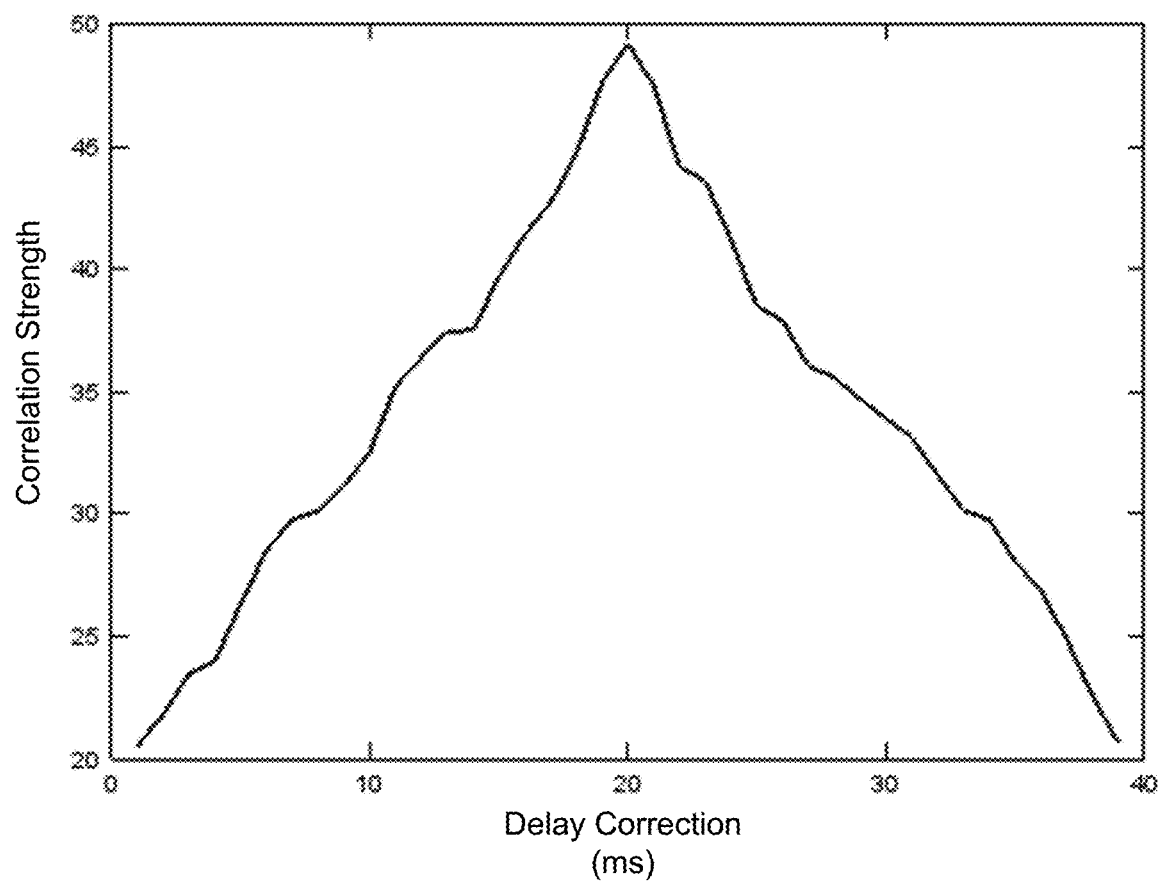
FIG. 18 illustrates a graph of data of correlation strength for time errors between two different sessions of data collection within a fluid distribution system according to examples of the present disclosure.

FIG. 18 illustrates graph 1800 of correlation strength for all possible time errors between two different sessions of data collection within a fluid distribution system according to examples of the present disclosure. In particular, graph 1800 is an example of selecting the correlation signal with a maximum correlation strength at 20 milliseconds, for example, as a time correction, from a range of 40 milliseconds (i.e. ±20 milliseconds maximum time error range), as discussed herein for FIG. 17.

It should also be understood that conditional language, such as, among others, "can," "could," "might," or "may," unless specifically stated otherwise, or otherwise understood within the context as used, is generally intended to convey that certain examples comprise, while other examples do not comprise, certain features, elements and/or steps. Thus, such conditional language is not generally intended to imply that features, elements, and/or steps are in any way required for one or more particular examples or that one or more particular examples necessarily comprise logic for deciding, with or without user input or prompting, whether these features, elements and/or steps are included or are to be performed in any particular example.

It should be emphasized that the above-described examples are merely possible examples of implementations and set forth for a clear understanding of the present disclosure. Many variations and modifications may be made to the above-described examples without departing substantially from the spirit and principles of the present disclosure. Further, the scope of the present disclosure is intended to cover any and all appropriate combinations and sub-combinations of all elements, features, and aspects discussed above. All such appropriate modifications and variations are intended to be included within the scope of the present disclosure, and all possible claims to individual aspects or combinations of elements or steps are intended to be supported by the present disclosure.

What is claimed is:

1. A method for analyzing data for a distribution pipe network within a fluid distribution system, comprising:
   receiving acoustic data from a plurality of nodes for a plurality of pipe segments;
   determining a characteristic frequency range for each pipe segment;
   decomposing the characteristic frequency range into a plurality of frequency sub-bands;
   building a leak sensitivity model based on the plurality of frequency sub-bands; and
   implementing a correlation schedule with the plurality of nodes based on a selection of the plurality of frequency sub-bands.

2. The method of claim 1, further comprising:
   receiving updated acoustic data from the plurality of nodes for each pipe segment;
   determining an updated frequency range for each pipe segment based on the updated acoustic data;
   creating an updated leak sensitivity model and an updated correlation schedule based on the updated frequency range and corresponding frequency sub-bands; and
   implementing the updated correlation schedule.

3. The method of claim 1, wherein each pipe segment comprises a section of the distribution pipe network between two nodes of the plurality of nodes.

4. The method of claim 1, wherein determining the characteristic frequency range for each pipe segment is based on a pipe material and a geometry for each pipe segment.

5. The method of claim 1, wherein implementing the correlation schedule comprises the steps of:
   downloading, by each node, the correlation schedule;
   synchronizing time for each node based on a reference time;
   recording an acoustic signal at each node for a same time and a same duration;
   reading and selecting a specific sub-band signal based on the correlation schedule;
   decimating and compressing the specific sub-band signal at each node; and
   transmitting a compressed sub-band signal from each node to a computing host.

6. The method of claim 5, wherein compressing the specific sub-band signal comprises a quantization method of absolute pulse code modulation utilizing a nonlinear function to compress the data to 1-bit.

7. The method of claim 5, wherein compressing the specific sub-band signal comprises utilizing 1-bit quantization.

8. The method of claim 5, further comprising:
   receiving, by the computing host, the compressed sub-band signal from each node;
   determining, by the computing host, correlation pairs based on adjacencies from each node, wherein the adjacencies are based on geographic information system data from each node; and
   detecting, by the computing host, coherent sources for each determined correlation pair by correlating the compressed sub-band signals of each correlation pair.

9. The method of claim 8, further comprising the steps of, responsive to a determination that the correlating of the compressed sub-band signals of a particular correlation pair is positive between a first node and a second node:
   determining, by the computing host, a time delay between the first node and the second node; and
   calculating, by the computing host, a leak location based on the time delay and the particular correlation pair.

10. A system for analyzing data for a distribution pipe network within a fluid distribution system, comprising:
    a computing host in communication with the fluid distribution system and configured to create a correlation schedule based on a selection of frequency sub-bands; and
    a plurality of nodes in communication with the computing host and configured to acquire acoustic data in the fluid distribution system, each node programmed to perform steps comprising downloading the correlation schedule;
synchronizing time with a reference time;
recording an acoustic signal, wherein each node records acoustic data at a same time and for a same duration;
reading the correlation schedule to determine a plurality of specific frequency sub-bands for each recording;
selecting a specific sub-band signal for each of the plurality of specific frequency sub-bands;
decimating the specific sub-band signal for each of the plurality of specific frequency sub-bands;
compressing the specific sub-band signal for each of the plurality of specific frequency sub-bands utilizing a quantization method; and
transmitting, as one file, a plurality of compressed sub-band signals to the computing host.

11. The system of claim 10, wherein selecting the specific sub-band signal for the specific frequency sub-band comprises the steps of:
decomposing the specific sub-band signal into a plurality of symmetric sub-bands; and
selecting only the specific frequency sub-band of the specific sub-band signal as determined by the correlation schedule.

12. The system of claim 10, wherein selecting the specific sub-band signal for the specific frequency sub-band comprises the steps of:
applying a pass-band filter to the specific sub-band signal to retain a desired energy in the specific sub-band signal.

13. The system of claim 10, wherein the quantization method comprises clipping to 1-bit compression.

14. The system of claim 10, wherein the quantization method comprises an absolute pulse code modulation utilizing a nonlinear function to compress the data to 1-bit.

15. The system of claim 10, wherein the quantization method comprises a non-linear pulse code modulation utilizing a nonlinear function.

16. The system of claim 10, wherein creating the correlation schedule by the computing host comprises the steps of:
receiving acoustic data from the plurality of nodes for a plurality of pipe segments;
determining a characteristic frequency range for each pipe segment;
decomposing the characteristic frequency range into a plurality of frequency sub-bands;
building a leak sensitivity model based on the plurality of frequency sub-bands by aggregating data from every pipe segment; and
configuring the correlation schedule to maximize sensitivity to leak detection of an acoustic propagation detection system based on the selecting of the specific sub-band signal for the specific frequency sub-band.

17. The system of claim 16, wherein the computing host is further configured to:
receive the compressed sub-band signal from each node;
determine correlation pairs based on adjacencies from each node, wherein the adjacencies are based on geographic information system data from each node; and
detect coherent sources for each determined correlation pair by correlating the compressed sub-band signals of each correlation pair.

18. A non-transitory computer-readable storage medium storing instructions that, when executed by a processing resource, cause the processing resource to perform steps comprising:
receiving acoustic data from a plurality of nodes for a plurality of pipe segments;
determining a characteristic frequency range for each pipe segment;
decomposing the characteristic frequency range into a plurality of frequency sub-bands;
building a leak sensitivity model based on the plurality of frequency sub-bands; and
implementing a correlation schedule with the plurality of nodes based on a selection of the plurality of frequency sub-bands.

19. The non-transitory computer-readable storage medium of claim 18, wherein implementing the correlation schedule comprises the steps of:
downloading, by each node, the correlation schedule;
synchronizing time for each node based on a reference time;
recording an acoustic signal at each node for a same time and a same duration;
reading and selecting a specific sub-band signal based on the correlation schedule;
decimating and compressing the specific sub-band signal at each node; and
transmitting a compressed sub-band signal from each node to a computing host.

20. The non-transitory computer-readable storage medium of claim 19, wherein compressing the specific sub-band signal comprises clipping to 1-bit compression.

* * * * *